United States Patent
Carroll et al.

(10) Patent No.: US 8,417,352 B2
(45) Date of Patent: Apr. 9, 2013

(54) SYSTEM AND METHOD FOR STIMULATING SENSORY NERVES

(75) Inventors: William J. Carroll, La Center, WA (US); Erling Jensen Aune, Jr., Vancouver, WA (US); Timothy J. Johnson, Camas, WA (US); Jens Olaf Roe Schouenborg, Lund (SE)

(73) Assignee: Meagan Medical, Inc., La Center, WA (US)

( * ) Notice: Subject to any disclaimer, the term of this patent is extended or adjusted under 35 U.S.C. 154(b) by 128 days.

(21) Appl. No.: 12/769,382

(22) Filed: Apr. 28, 2010

(65) Prior Publication Data

US 2010/0274327 A1 Oct. 28, 2010

Related U.S. Application Data

(63) Continuation-in-part of application No. 11/253,936, filed on Oct. 19, 2005, now Pat. No. 8,086, 322.

(60) Provisional application No. 60/624,500, filed on Oct. 19, 2004.

(51) Int. Cl.
*A61N 1/00* (2006.01)
*A61B 5/04* (2006.01)

(52) U.S. Cl.
USPC ............ 607/115; 607/9; 600/372; 600/373; 600/377; 600/382; 600/390; 600/393

(58) Field of Classification Search .............. 607/9, 115; 600/372–373, 377, 382, 396, 393
See application file for complete search history.

(56) References Cited

U.S. PATENT DOCUMENTS

| 4,793,353 A | * | 12/1988 | Borkan ........................... 607/60 |
| 4,837,049 A | | 6/1989 | Byers et al. |
| 4,867,166 A | | 9/1989 | Axelgaard et al. |
| 4,920,968 A | | 5/1990 | Takase |
| 4,969,468 A | | 11/1990 | Byers et al. |
| 5,350,414 A | * | 9/1994 | Kolen ............................. 607/62 |
| 5,449,378 A | * | 9/1995 | Schouenborg .................. 607/46 |
| 5,772,688 A | | 6/1998 | Muroki |
| 5,928,144 A | | 7/1999 | Real |
| 6,044,286 A | | 3/2000 | Ogama |
| 6,083,253 A | | 7/2000 | Ogama |
| 6,277,116 B1 | * | 8/2001 | Utely et al. ..................... 606/42 |
| 6,609,018 B2 | | 8/2003 | Cory et al. |
| 6,690,959 B2 | | 2/2004 | Thompson |
| 6,785,569 B2 | | 8/2004 | Schmidt et al. |
| 6,821,281 B2 | | 11/2004 | Sherman et al. |

(Continued)

FOREIGN PATENT DOCUMENTS

| CA | 2584722 | 7/2005 |
| CN | 101124010 | 2/2008 |

(Continued)

*Primary Examiner* — Nicole F Lavert
(74) *Attorney, Agent, or Firm* — Blank Rome LLP

(57) ABSTRACT

An electrotherapy system for stimulating sensory nerves within skin tissue includes a electrode carrier, a pulse generator, an array of skin-penetrating electrodes and surface skin electrodes, a pulse conditioning circuit, and a power source. The system administers biphasic pulsed current at the surface skin electrodes and monophasic pulsed current at each skin-penetrating electrode. The skin-penetrating surfaces and skin contact surfaces of the electrotherapy system may be sterilized or may be replaceable for outpatient reusability.

26 Claims, 16 Drawing Sheets

U.S. PATENT DOCUMENTS

| | | |
|---|---|---|
| 6,918,907 B2 | 7/2005 | Kelly et al. |
| 7,212,865 B2 | 5/2007 | Cory |
| 7,457,667 B2 | 11/2008 | Skiba |
| 2002/0028991 A1 | 3/2002 | Thompson |
| 2002/0120260 A1 | 8/2002 | Morris |
| 2002/0120261 A1 | 8/2002 | Morris et al. |
| 2003/0050548 A1 | 3/2003 | Schmidt et al. |
| 2004/0164454 A1 | 8/2004 | Gartstein et al. |
| 2004/0181216 A1 | 9/2004 | Kelly et al. |
| 2005/0043775 A1 | 2/2005 | John et al. |
| 2005/0075670 A1* | 4/2005 | Bengtsson .................. 607/3 |
| 2005/0203366 A1 | 9/2005 | Donoghue et al. |
| 2006/0047194 A1 | 3/2006 | Grigorov |
| 2006/0085056 A1 | 4/2006 | Schouenborg |
| 2006/0111626 A1 | 5/2006 | Rossing et al. |
| 2006/0149341 A1 | 7/2006 | Palti |
| 2006/0173261 A1 | 8/2006 | Kall et al. |
| 2007/0015984 A1 | 1/2007 | Yeo et al. |
| 2007/0106359 A1 | 5/2007 | Schaer et al. |
| 2007/0123766 A1 | 5/2007 | Whalen et al. |
| 2007/0169333 A1 | 7/2007 | Donoghue et al. |
| 2007/0238944 A1 | 10/2007 | Axelgaard |
| 2007/0265692 A1 | 11/2007 | Koop et al. |
| 2007/0270927 A1 | 11/2007 | Fisk |
| 2007/0276318 A1 | 11/2007 | Henley |
| 2010/0264097 A1* | 10/2010 | Sun et al. ................ 210/767 |
| 2011/0082413 A1* | 4/2011 | Ready et al. ............... 604/20 |

FOREIGN PATENT DOCUMENTS

| | | |
|---|---|---|
| EP | 0275642 A1 | 7/1988 |
| EP | 05794744 | 10/2005 |
| HK | 1118024 | 1/2009 |
| JP | 01164373 A | 6/1989 |
| JP | 2008516724 | 5/2008 |
| JP | 2009202020 A | 9/2009 |
| KR | 10200701127 | 11/2007 |
| WO | 9323112 A1 | 11/1993 |
| WO | 2006043885 | 4/2006 |
| WO | 2007136657 A2 | 11/2007 |

\* cited by examiner

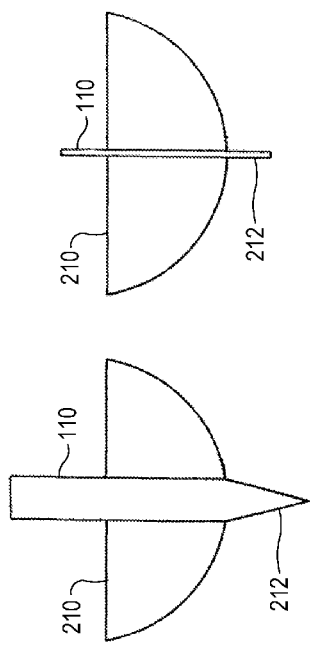
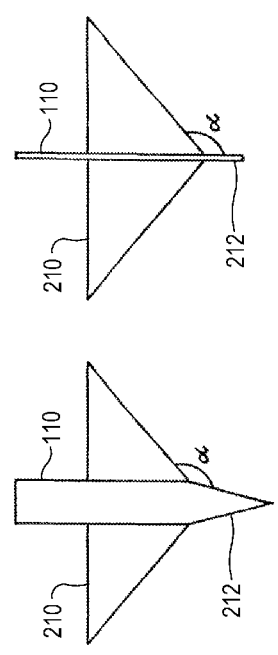
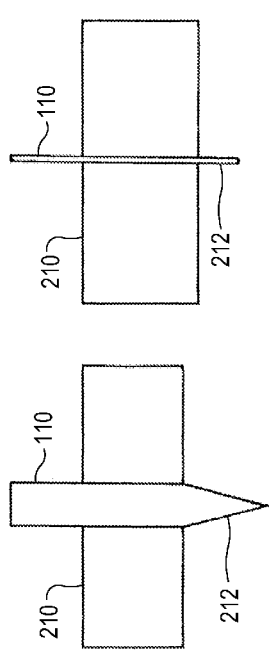

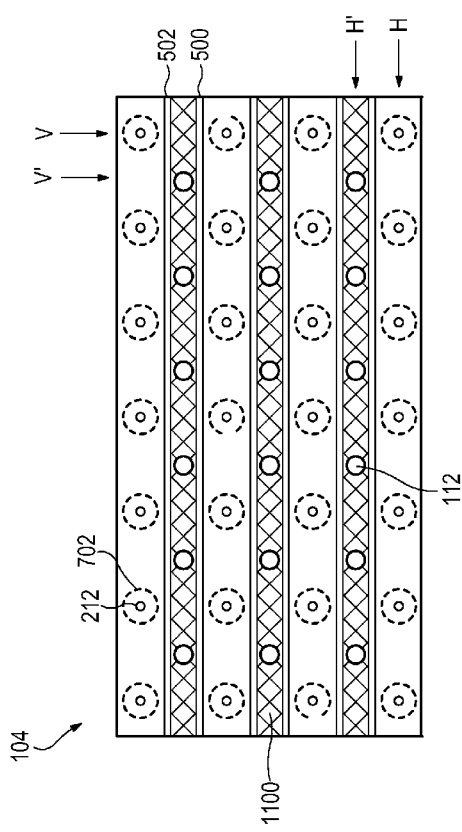
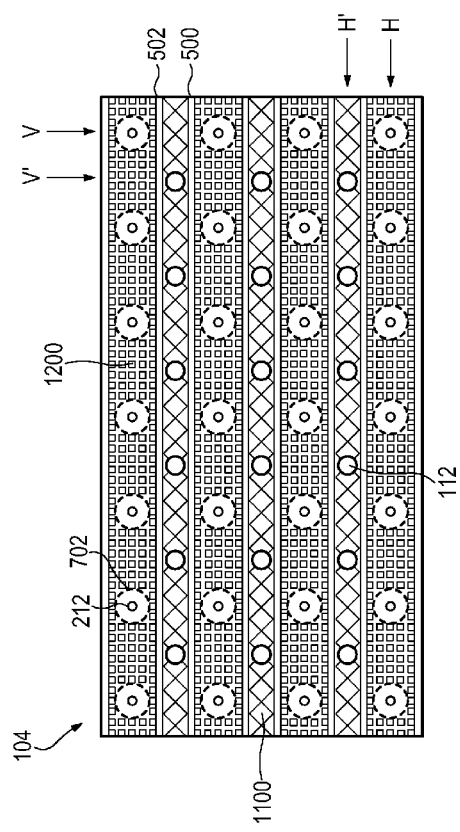
FIG. 11
FIG. 12

US 8,417,352 B2

SYSTEM AND METHOD FOR STIMULATING SENSORY NERVES

RELATED INVENTIONS

The present patent application is a continuation-in-part of co-pending U.S. patent application Ser. No. 11/253,936 filed Oct. 19, 2005 now U.S. Pat. No. 8,086,322, published as US 2006/0085056 A1, currently pending, which claims priority from U.S. Provisional Patent Application Ser. No. 60/624,500, filed Oct. 19, 2004, the disclosures of which are incorporated entirely herein by reference.

FIELD OF THE INVENTION

The present invention relates to electrical stimulation of cutaneous sensory receptors and, more particularly, to an electrotherapy system for outpatient use having reusable skin-penetrating electrodes and surface skin electrodes for stimulating sensory nerves within skin tissue.

BACKGROUND OF THE INVENTION

Electroanalgesic therapies are known nonpharmacologic alternatives to conventional analgesic drugs for the management of acute and chronic pain. For example, percutaneous electrical nerve stimulation (PENS) is a known form of electroanalgesic therapy typically used for the treatment of intractable pain associated with chronic low back pain syndrome by stimulating the spinal cord using electrodes implanted percutaneously into the epidural space. The term PENS has also been used to describe a technique for inserting 32-gauge acupuncture needles into soft tissues or muscles to electrically stimulate peripheral nerve fibers in the sclerotomal, myotomal, or dermatomal distribution corresponding to a patient's pain symptoms. Medical devices having arrays of percutaneous electrodes that utilize microstructure needles, which are less invasive than deeper-penetrating acupuncture needles, have also been used for delivering PENS. The microstructure needles provide sufficient penetration to overcome the electrical impedance of the skin tissue for effectively recruiting sensory fibers.

As the understanding of the topographical organization of nociceptive systems becomes more detailed, the target location of the stimulation, the percutaneous electrodes' depth of penetration, and the current amplitude become more exacting. Percutaneous neuromodulation therapy (PNT) and cutaneous field stimulation (CFS) are specific forms of PENS that have been developed using that understanding. PNT is used for the treatment of cervical and lumbar pain and utilizes longer, acupuncture-type needles having a depth of penetration into the skin tissue of up to 3 cm. And, CFS is used more generally to treat pain and itch and utilizes an array of microstructure needles introduced close to the nerve endings in the skin. Because of the stringent requirements established for needle electrodes by the Food and Drug Administration (FDA) regarding the packaging, sterilization, reuse, and disposal of such electrodes, treatments utilizing such electrodes have generally been administered under the supervision of a physician (e.g., in a doctor's office or a clinic).

CFS is used to assist in the management of chronic nociceptive and neuropathic pain based on the understanding that specific types of sensory nerves that are linked to diminishing the perception of pain can be activated by low amplitude, long duration electrical stimulation if electrodes having sharp tips (i.e., microstructure needles) are introduced close to the nerve endings in the skin. CFS treatment also influences specific active components necessary for perceiving itch by inducing long lasting inhibitory mechanisms in central pathways and by actually normalizing the number of epidermal sensory fibers in itchy skin. Accordingly, CFS also provides an alternative to known treatments for localized itch.

The sensory receptors stimulated by CFS are axons within the skin tissue known as nociceptors, specifically $A\delta$ and C nerve fibers. The stimulation of $A\delta$ and C nerve fibers, although effective in diminishing the perceptions of both pain and itch, can be a relatively uncomfortable treatment because a prickling and/or burning sensation is perceived from the stimulation of the $A\delta$ and C nerve fibers, which can be painful. Because the aversiveness of $A\delta$ and C nerve fiber stimulation can be masked by $A\beta$ fiber stimulation, it would be a considerable advantage to combine $A\beta$ fiber stimulation (e.g., transcutaneous electrical nerve stimulation (TENS)) and $A\delta$ and C fiber stimulation (e.g., CFS) in the same equipment. Accordingly, there is a need for a method and device that combines $A\beta$ fiber stimulation and $A\delta$ and C fiber stimulation in one treatment. Moreover, there is a need for a method and device that combines TENS and CFS in one treatment.

BRIEF DESCRIPTION OF THE DRAWINGS

Many aspects of the present invention can be better understood with reference to the following drawings, which are part of the specification and represent preferred embodiments of the present invention. The components in the drawings are not necessarily to scale, emphasis instead being placed upon illustrating the principles of the present invention. And, in the drawings, like reference numerals designate corresponding parts throughout the several views.

FIGS. 3A through 3F are elevational views taken in section of different non-limiting embodiments of skin-penetrating electrodes with stop nodules according to the present invention;

FIG. 11 is a plan view of the front face of the electrode carrier of FIG. 5 in accordance with a non-limiting embodiment of the present invention;

FIG. 12 is a plan view of the front face of the electrode carrier of FIG. 5 in accordance with another non-limiting embodiment of the present invention;

DETAILED DESCRIPTION OF THE PREFERRED EMBODIMENTS

Non-limiting embodiments of the present invention will now be described in detail, by way of example, with reference to the drawings.

Figure 1:
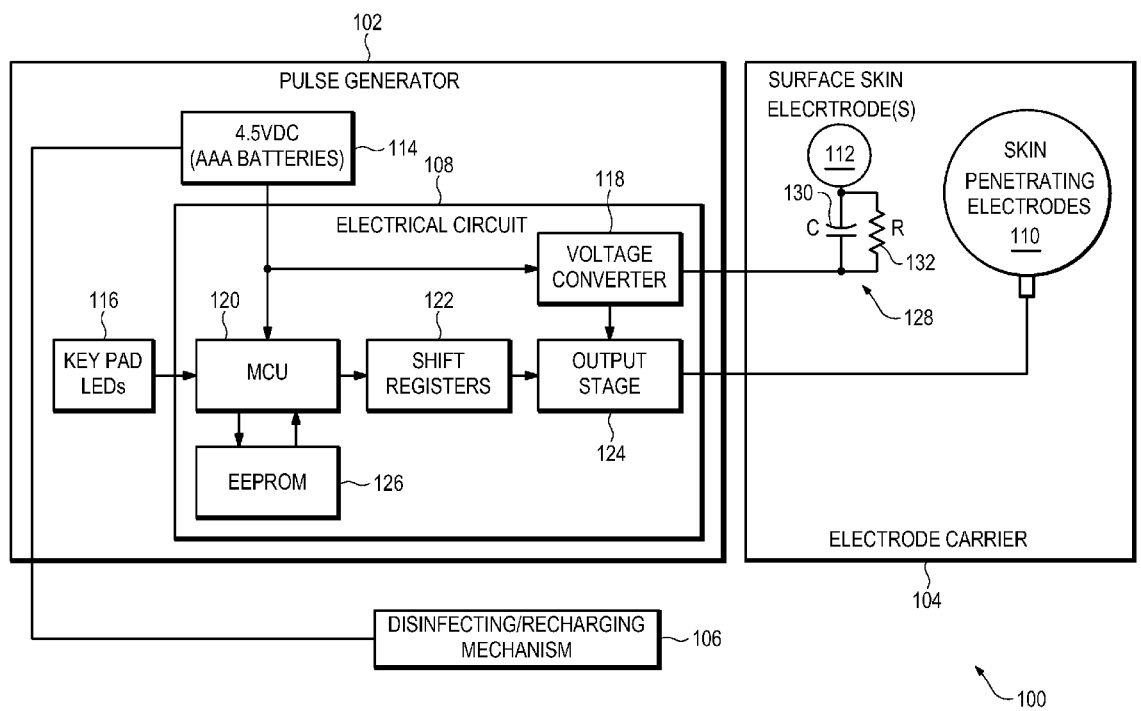
FIG. 1 is a schematic view of an electrotherapy system in accordance with a non-limiting embodiment of the present invention.

Turning to the figures, FIG. 1 illustrates a non-limiting embodiment of an electrotherapy system 100 for stimulating sensory nerves within skin tissue. The electrotherapy system 100 includes a multi-channel pulse generator 102, an electrode carrier 104, and a combination disinfecting/recharging mechanism 106. The pulse generator 102 includes an electrical circuit 108 that is configured to transmit pulsed currents into a patient's skin via skin-penetrating electrodes 110 (e.g., percutaneous electrodes) and surface skin electrode(s) 112 (e.g., conductive plate electrodes) disposed on the electrode carrier 104. The skin penetrating electrodes 110 are configured to apply electrical stimulation (i.e., electro-stimulation) percutaneously to Aδ and C nerve fibers, and the surface skin electrode(s) 112 are configured to apply electrical stimulation transcutaneously to Aβ nerve fibers prior to and/or overlapping in time with the electrical stimulation applied to the Aδ and C nerve fibers. And, the disinfecting/recharging mechanism 106 functions to reduce microbial reproduction on the skin-penetrating surfaces of the skin-penetrating electrodes 110 and the skin-contacting surfaces of the electrode carrier 104 and the surface skin electrode(s) 112 in between treatment applications. The disinfecting/recharging mechanism 106 may also function to recharge the pulse generator's 102 power source 114 in between treatment applications, concurrently with or separate from its disinfecting operation.

Multi-Channel Pulse Generator 102

As FIG. 1 illustrates, the multi-channel pulse generator 102 includes an electrical circuit 108, a power source 114, and a key pad 116. The electrical circuit 108 includes a voltage converter 118, a microcontroller unit (MCU) 120, shift registers 122, an output stage 124, and an electrically erasable programmable read-only memory (EEPROM) 126. The voltage converter 118 is a one Megahertz oscillator that feeds a voltage multiplier circuit (not shown) to boost the power source 114 voltage to approximately 50 Volts. Any suitable voltage converter 118 that converts complementary metal-oxide-semiconductor (CMOS) logic to analog may be used. The MCU 120 monitors the key pad 116 input, provides timing sequence to the shift registers 122, and executes instructions from the firmware stored in the EEPROM 126. The MCU 120 may be PIC-based. The shift registers 122 provide the logic used for clocking the output pulse timing to the output stage 124. The output stage 124 includes a series of transistors that couple the power source 114 voltage to the electrode carrier 104.

Memory is stored via the EEPROM 126. The EEPROM 126 can be any suitable nonvolatile memory device. Also, the EEPROM 126 may provide memory storage for a data logging function (not shown). The data logging function can be used to record treatment uses, durations, amplitude outputs, and other user/patient/subject information, such that a manufacturer, a sponsor of a clinical investigation, or a prescribing physician may query the EEPROM 126 to obtain that information. Other non-limiting configurations of the pulse generator 102 and firmware may also be employed by the present invention. And, the pulse generator's 102 components may be further integrated into a field programmable gate array (not shown) with internal flash memory.

As FIG. 1 illustrates, the power source 114 is made up of three AAA 1.5 Volt alkaline batteries which provide approximately 5 to 50 Volts per channel, but the power source 114 may be any conventional rechargeable battery or batteries, including rechargeable lithium polymer batteries (not shown). The power source 114 may also be any other suitable voltage source, such as a conventional outlet plug, solar panel, etc.

As FIG. 1 also illustrates, a pulse conditioning circuit 128 is provided between the pulse generator 102 and the surface skin electrode(s) 112. The pulse conditioning circuit 128 may be disposed on the electrode carrier 104. The pulse conditioning circuit 128 allows more accurate positioning of the active portions of the skin-penetrating electrodes 110 for effectively stimulating Aδ and C nerve fibers. Several factors effect whether the skin-penetrating electrodes 110 will generate a sufficient voltage gradient to effectively stimulate Aδ and C nerve fibers. For example, load varies based on the skin-penetrating electrode's 110 distance from a nerve, with impedance decreasing as the needle tip approaches the nerve, and the resistance/capacitance of a patient's skin tissue may differ between patients or for different skin locations on the same patient. Thus, the voltage gradient created by the skin-penetrating electrodes 110 is unpredictable and highly dependent on the positioning of the skin-penetrating electrodes 110.

In order to provide a predictable voltage gradient for different loads and different skin resistances/capacitances, the pulse conditioning circuit 128 is placed in series with the electrical path through a patient's skin to maintain the desired voltage gradient to effectively stimulate Aδ and C nerve fibers. To create that electrical path, one or more surface skin electrodes 112 can be employed with the reverse polarity of the skin-penetrating electrodes 110 so that it operates as a collector for the skin-penetrating electrodes 110. In that configuration, the pulse conditioning circuit 128 is located on the return electrical pathway between the surface skin electrode 112 and the pulse generator 102. In the alternative, one or more skin-penetrating electrodes 110 can operate as a collector for the other skin-penetrating electrodes 110.

The pulse conditioning circuit 128 maintains the desired voltage gradient by maintaining a constant waveform across the skin-penetrating electrodes 110 and the collector electrodes. Preferably, the pulse conditioning circuit 128 is configured to approximate a relatively rectangular waveform (e.g., FIGS. 17 and 18) when delivered through the patient's skin tissue. And, the pulse conditioning circuit 128 maintains a constant waveform by maintaining a linear relationship between the voltage and current components of the waveform based on the impedance characteristics of the patient's skin tissue. But, as discussed above, the electrical characteristics of skin tissue may change between patients or even between locations on a single patient's skin. Accordingly, the characteristics of the pulse conditioning circuit 128 may also need to change.

Although FIG. 1 illustrates the pulse conditioning circuit 128 as a capacitor 130 in parallel with a resistor 132, a more complex circuit can be employed. For example, the pulse conditioning circuit may include a semiconductor field effect transistor, a digital signal processor, an inductor, and other active semiconductor components so that the circuit characteristics of the pulse conditioning circuit 128 can be adjusted to maintain the desired waveform across patients' skin tissue as the electrical characteristics of the patients' skin tissue change. Accordingly, the pulse generator 102 may also include a circuit (not shown) for measuring values of voltage and current across a patient's skin tissue to determine the impedance of the patient's skin. Based on that measurement, a digital computer (not shown) in the pulse generator 102 can be used to automatically adjust the components of the pulse conditioning circuit to maintain the desired waveform through the patient's skin as the impedance of the skin tissue fluctuates, thereby maintaining the desired voltage gradient. In the alternative, the patient can adjust the circuit characteristics of the pulse conditioning circuit 128 manually.

The key pad 116 may be any suitable operator key pad for patient input having a display to indicate the status and output of the electrotherapy system 100. The key pad 116 provides a user interface to control the programming and function of the pulse generator 102. As illustrated, for example, in FIG. 2, the key pad 116 may include positive and negative toggle keys 200 for controlling the amount of electro-stimulation output, a series of LEDs 202 for displaying the level of electro-stimulation output, and a power button 204 for turning the electrotherapy system 100 on and off.

Figure 2:
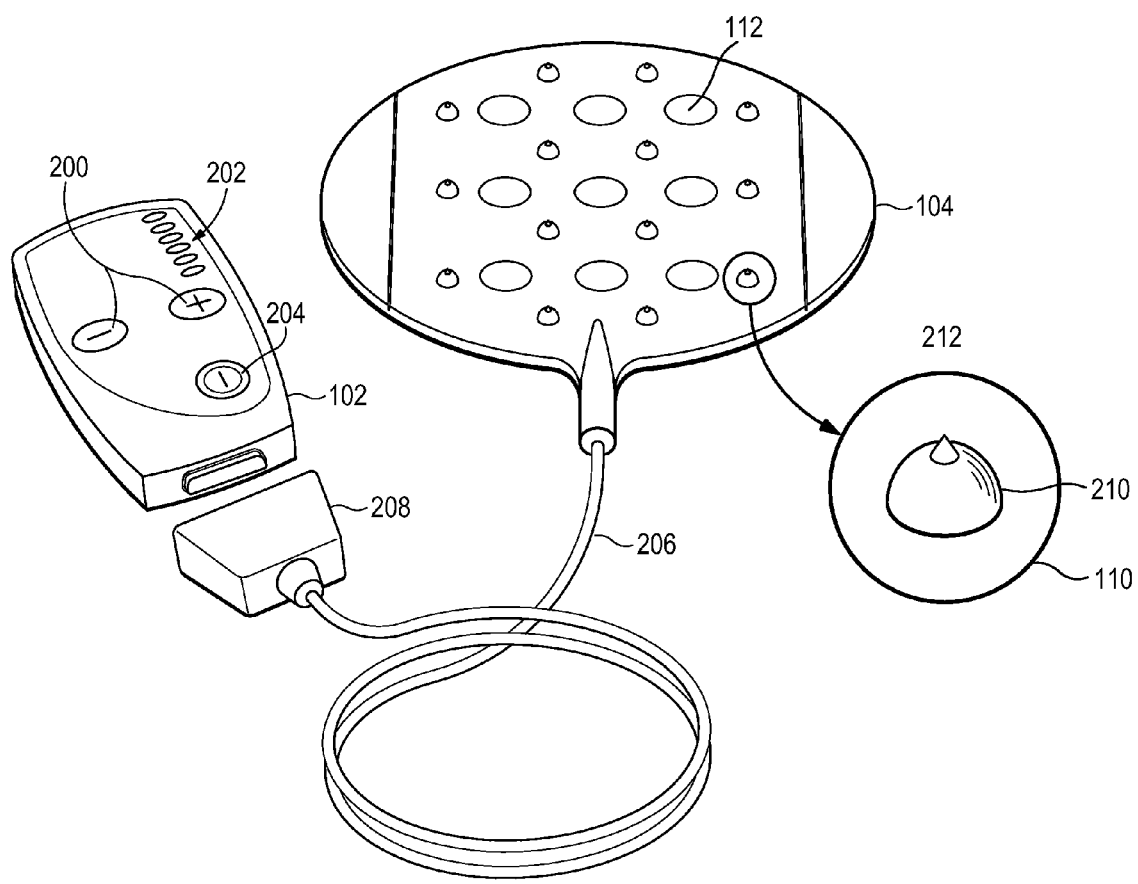
FIG. 2 is an isometric view a pulse generator and electrode carrier in accordance with a non-limiting embodiment of the invention.

As illustrated in FIG. 2 illustrates, the pulse generator 102 is provided physically separate but electrically connected to the electrode carrier 104 by an electrode cable 206. A cable-plug assembly 208 is provided to detachably connect the pulse generator 102 to the surface skin electrode(s) 112 and the skin-penetrating electrodes 110 via the electrode cables 208. The output stage 124 of the electrical circuit 108 may be disposed on the electrode carrier 104 or in the pulse generator 102. The pulse generator 102 may be constructed in a housing made of any suitable material, such as a polycarbonate/ABS blend, when it is provided physically separate from the electrode carrier 104. In the alternative, the pulse generator 102 may be formed or mounted on the rear face of electrode carrier 104 (e.g. FIG. 13).

The embodiment of the electrode carrier 104 illustrated in FIG. 2 includes two rows of three and two rows of four skin-penetrating electrodes 110 with three rows of three surface skin electrodes 122 interspersed therebetween. Thus, that electrode carrier 104 includes an array of fourteen (14) skin-penetrating electrodes 110 and nine (9) surface skin electrodes 112. Each individual skin-penetrating electrode 110 and each individual surface skin electrodes 112 is electrically connected to the pulse generator via a separate channel for effecting current transfer through each of the electrodes 110 and 112. Accordingly, in the embodiment illustrated in FIG. 2, the multi-channel pulse generator 102 includes at least twenty-three channels (one for each of the fourteen skin-penetrating electrodes 110 and one for each of the nine surface skin electrodes 112). The pulse generator 102 can be similarly configured for virtually any number of electrodes 110 and 112 and corresponding channels.

Electrode Carrier 104

The electrode carrier 104 is made of thin and flexible, but not extendable or compressible, polycarbonate. The electrode carrier 104 is substantially flat yet conformable and shapeable to the skin tissue such that it can be applied to most body parts. It is also possible for the electrode carrier 104 to be made of less pliable, polymer materials in order to provide more rigidity. For example, the electrode carrier 104 can be a printed circuit board (PCB), as conventionally known in the fabrication and manufacture of appliances for electro-stimulation and in the delivery and administration of electrotherapy.

As FIG. 2-5 illustrate, each of the skin-penetrating electrodes 110 is embedded in a stop nodule 210 so that only a skin-penetrating portion 212 extends from the annular surface of the stop nodule 210. The stop nodules 210 advance the skin-penetrating portion 212 of the skin-penetrating electrodes 110 further toward a patient's skin tissue by functioning as a spacer between the front side of the electrode carrier 104 and a patient's skin. The stop nodule 210 also enables the skin-penetrating portions 212 of the skin-penetrating electrodes 110 to penetrate a patient's skin a predetermined depth when pressure is applied from above by providing a blunt contact surface that makes contact with the patient's skin and stops the skin-penetrating portion 212 from penetrating the patient's skin any further beyond that point of contact.

To provide a blunt enough contact surface to control the depth that the skin-penetrating portion 212 of the skin-penetrating electrodes 110 penetrates a patient's skin, the stop nodules 210 have a cross-sectional surface area of about 0.2 to 25 $mm^2$, preferably about 3 $mm^2$. The distal end of each stop nodule 210 is preferably a convex shape to provide the optimal amount of skin contact for controlling the depth that the skin-penetrating portion 212 of the skin-penetrating electrodes 110 penetrates a patient's skin. For example, the distal end of the stop nodule 210 may be domed (e.g., FIGS. 2, 3A, 3B, and 4), conical (e.g., FIGS. 3C and 3D), or substantially flat (e.g., FIGS. 3E, 3F, 5, 6A, and 6B). When the distal end of the stop nodule 210 is conical, the angle $\alpha$ between the skin-penetrating portion 212 of the skin-penetrating electrode 110 and the stop nodule 210 preferably does not exceed 160° for satisfactorily controlling the depth that the skin-penetrating portions 212 of the skin-penetrating electrodes 110 penetrate a patient's skin. Larger angles $\alpha$ result in a greater depth of skin penetration.

The cross-sectional surface area of each skin-penetrating portion 212 should be sufficiently small such that it will penetrate a patient's skin under the exertion of pressure without causing significant skin injuries. Accordingly, the cross-sectional surface of the skin-penetrating electrodes 110 should be about 0.065 to 0.4 $mm^2$. The tip of each skin-penetrating portion 212 may be pointed at an angle less than 90°, preferably less than 45°, to further reduce skin injuries. The tips of the skin-penetrating portions 212 may be perfectly conical (e.g., FIGS. 2, 3A, 3C, 3E, 4, 5, 6A, and 6B) or convexly/concavely conical pointed (e.g., FIGS. 7, 14, and 15), they may have a cutting edge (not shown), or they may have the shape of a needle or a pin (e.g., FIGS. 3B, 3D, and 3F).

The skin-penetrating electrodes 110 are also designed to penetrate a patient's skin sufficiently to achieve the desired stimulation of skin receptors. More particularly, the skin-penetrating portions 212 of the skin-penetrating electrodes 110 have a sufficiently small non-insulated, "active" surface area for providing the high electrical current density required to activate and recruit Aδ and C nerve fibers, but are long enough to reach a depth of skin penetration at which Aδ and C nerve fibers can be activated and recruited. Accordingly, when the overall length required to reach the desired depth of skin penetration results in too much active surface area on the skin-penetrating portions 212, it may be necessary to insulate a portion of the skin-penetrating portions 212 along their length so that only a small active surface area is exposed at their tips (e.g., FIGS. 14 and 15). The active length of the skin-penetrating portions 212 should be about 0.1 to 0.5 mm.

The depth of skin penetration desired will depend on the type of skin being treated and the location of the Aδ and C nerve fibers being targeted. And, because the stop nodules 210 advance the skin-penetrating portions 212 of the skin-penetrating electrodes 110 further toward a patient's skin tissue, different combinations of dimensions for the stop nodules 210 and the skin-penetrating portions 212 may be used to achieve that desired depth. For example, the skin-penetrating portions 212 of the skin-penetrating electrodes 110 may have a length from base to tip of about 0.1 to 5.0 mm, preferably about 0.2 to 3.0 mm, and the stop nodules 210 may have a height from base to distal end of about 0.1 to 5.0 mm. Moreover, both the heights and cross-sectional surface areas of the stop nodules 210 may be changed depending on the electrode density and the curvature of the skin tissue being treated to help achieve the desired depth of penetration.

The stop nodules 210 may be made of non-conductive material, such as UV stabilized polycarbonate/ABS, so that current is only transferred to a patient's skin via the skin-penetrating portions 212 of the skin-penetrating electrodes 110. If the stop nodules 210 are made of an electrically conductive material, the skin-penetrating portions 212 of the skin-penetrating electrodes 110 should be electrically insulated from the stop nodules 210. The skin-penetrating electrodes 110 may be made from silver, platinum and other noble metals, stainless steel blanks, commercially available stainless steel hypodermic needles cut and shaped to a desired length, and combinations thereof. The skin-penetrating electrodes 110 may further be plated with conductive metals if desired. The stop nodule 210 may be molded around the skin-penetrating electrode 110 or formed separately and later assembled with the skin-penetrating electrode 110 such that the skin-penetrating electrodes 110 are removable and replaceable in the electrode carrier 104.

The surface skin electrodes 112 may be any suitable conventional surface skin electrode with an adhesive interface for application to skin tissue. Such surface skin electrodes 112 are conventionally known for use in applying transcutaneous electrical nerve stimulation (TENS). The surface skin electrodes 112 can be made of metal, carbonized silicon, or other conductive polymers. The surface skin electrodes 112 should have a large conductive diameter to provide the lower electrical current densities required to activate and recruit Aβ fibers. For example, the surface skin electrodes 112 should have a surface area, or a combined surface area for linked rows H' or columns V' (e.g., FIGS. 9 and 10), of more than 100 mm². The surface skin electrodes 112 can act as return or collector electrodes of opposite polarity from the skin-penetrating electrodes 110 or other surface skin electrodes 112 during the application and delivery of electrotherapy and electro-stimulation.

The array of skin-penetrating electrodes 110 may be of substantially any shape, including asymmetrical arrangements, and may include one hundred skin-penetrating electrodes 110 or more. Such arrays may include a plurality of surface skin electrodes 112 interspersed between the skin-penetrating electrodes 110 (e.g., FIGS. 2, 4, and 5) on the electrode carrier 104 or as a frame surrounding the perimeter of the skin-penetrating electrodes 110 on the electrode carrier 104 (not shown). The surface skin electrodes 112 should be sized and spaced relative to the skin-penetrating electrodes 110 based on the size of the array of skin-penetrating electrodes 110 and the number of skin-penetrating electrodes 110.

Figure 4:
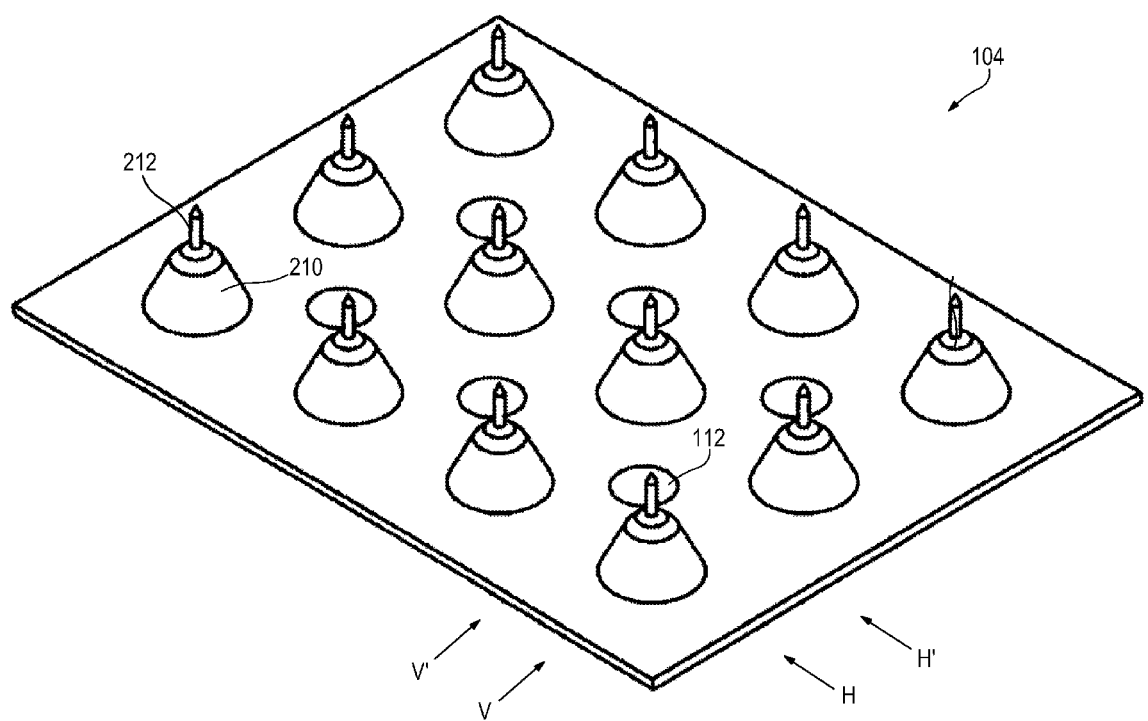
FIG. 4 is an isometric view of an electrode carrier in accordance with a non-limiting embodiment of the present invention.
Figure 5:
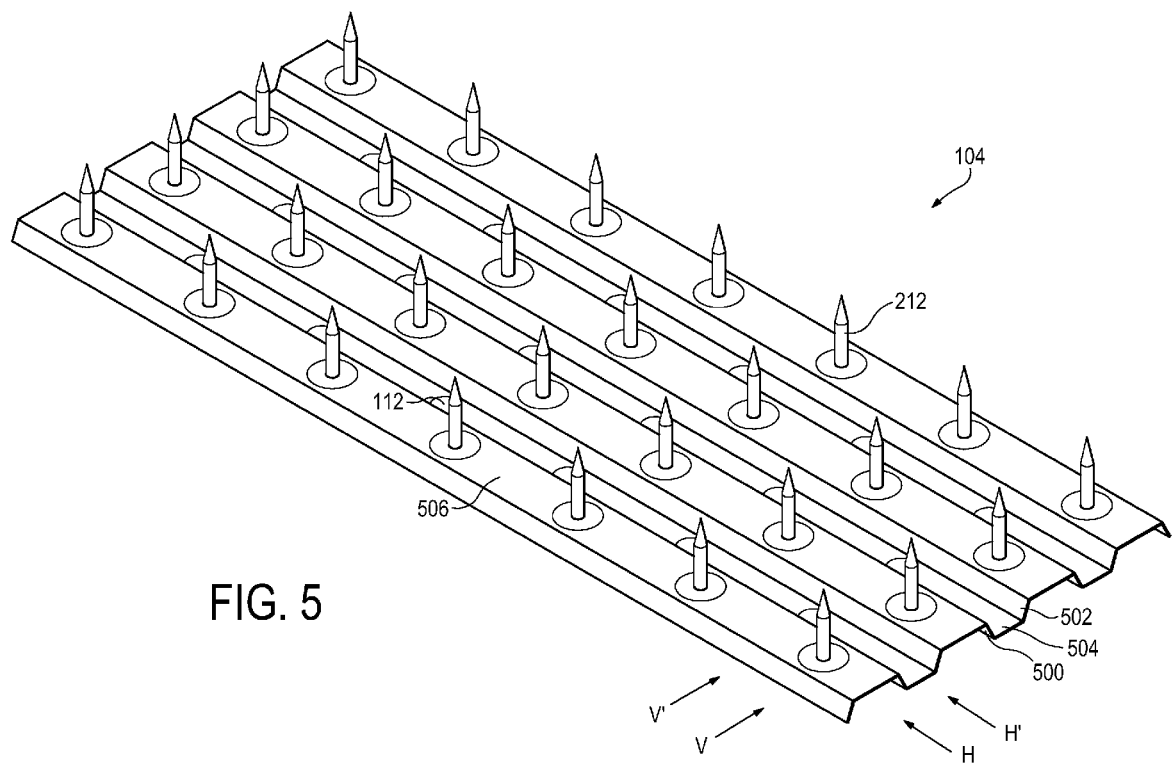
FIG. 5 is an isometric view of an electrode carrier in accordance with another non-limiting embodiment of the present invention.

As FIGS. 4 and 5 illustrate, the skin-penetrating electrodes 110 may be disposed on the electrode carrier 104 in a rectangular array defined by columns V and rows H that are spaced apart from one another by about 10 mm or more so as to form a field of stimulation. The surface skin electrodes 112 may be disposed on the electrode carrier 104 in a rectangular array defined by columns V' and rows H' disposed between the columns V and rows H of skin-penetrating electrodes 110. The horizontal distance between each surface skin electrode 112 and its neighboring skin-penetrating electrode 110 may be about 1 to 30 mm. If the surface skin electrode 112 is not disposed on the electrode carrier 104 with the skin-penetrating electrodes 110, the surface skin electrode 112 should be positioned at a distance close enough to the array of skin-penetrating electrodes 110 for the surface skin electrode 112 to serve as a collector for the electro-stimulation applied via the array of skin-penetrating electrodes 110. And, instead of extending from stop nodules 210 to advance the skin-penetrating portions 212 further toward a patient's skin tissue as illustrated, for example, in FIG. 4, the skin-penetrating portions 212 may also extend from raised crest sections 506 as illustrated, for example, in FIG. 5.

In FIG. 5, side walls 500 and 502 are formed in the electrode carrier 104 on opposite sides of each row H of skin-penetrating electrodes 104 so as to form valley sections 504 and the crest sections 506. The surface skin electrodes 112 are disposed in the valley sections 504 between side walls 500 and 502 and the skin-penetrating electrodes 110 are disposed on the crest sections 506 above the surface skin electrodes 112. Accordingly, just as with skin-penetrating electrodes 110 extending from stop nodules 210 (e.g., FIG. 4), when the electrode carrier 104 is applied to a patient's skin by exerting pressure on its rear face, the skin-penetrating electrodes 110 disposed on the crest sections 506 will extend further toward the surface of the patient's skin. The side walls 500 and 502 may be constructed of stretchable material such that they bend and the electrode carrier 104 conforms to the skin tissue of a patient's various curved body parts, such as the knees, elbows, feet. And, the side walls 500 and 502 may be substantially straight (e.g., FIG. 5) or they may be curved (e.g., FIG. 14).

Figure 6A:
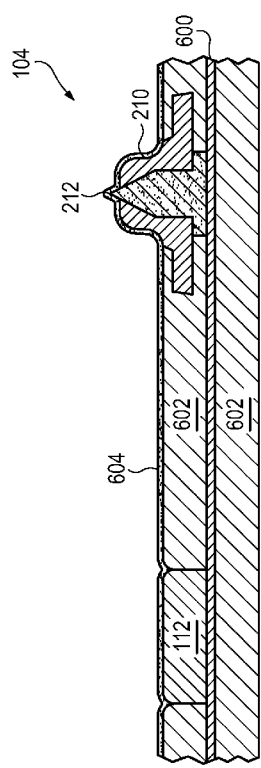
FIGS. 6A and 6B are elevational views taken in section of a one-piece electrode carrier comprising an antimicrobial agent according to non-limiting embodiments of the invention.
Figure 6B:
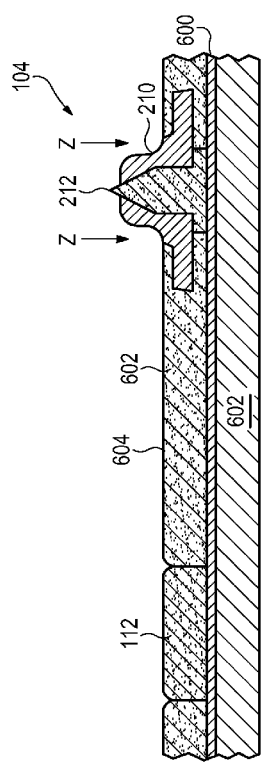
Figure 7:
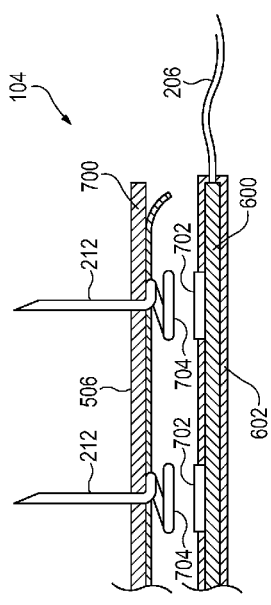
FIG. 7 is an elevational view taken in section of a two-piece electrode carrier comprising a circuit board and disposable interface in accordance with a non-limiting embodiment of the present invention.
Figure 8:
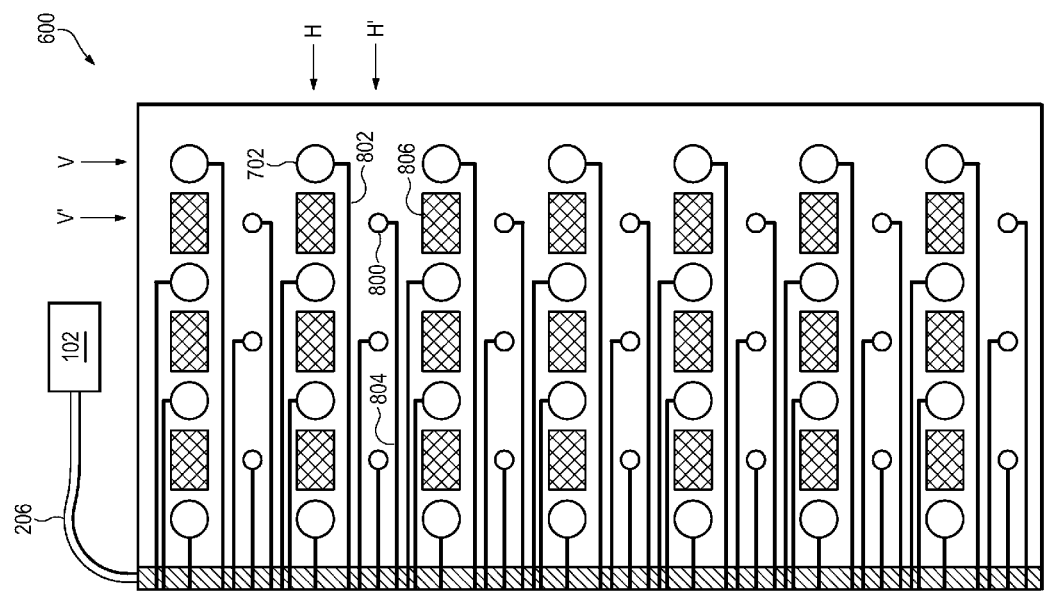
FIG. 8 is a plan view of the front face of an embodiment of the circuit board of FIG. 5.

As FIGS. 6 and 7 illustrate, the electrode carrier 104 comprises a circuit board 600 surrounded by a non-conductive coating 602. The skin-penetrating electrodes 110 and surface skin electrodes 112 are disposed in the non-conductive coating 602 and electrically coupled to the circuit board 600. The circuit board 600 electrically couples the skin-penetrating electrodes 110 and surface skin electrodes 112 to the pulse generator 102 via traces 802 and 804 (FIGS. 8-10) screen-printed on the circuit board 600, via individually insulated wires, or via any other suitable electrical connection. The non-conductive coating 602 is provided as a substrate pad surrounding the electrode carrier 104 to prevent current from passing into a patient's skin from any conductive element of the electrode carrier 104 other than the skin-penetrating electrodes 110 and/or surface skin electrodes 112. And, by surrounding the circuit board 600 with a non-conductive coating 602, any electrical components disposed on the circuit board 600 are protected from damage during certain disinfecting operations, such as boiling or autoclaving.

The non-conductive coating 602 may be made of any non-conductive thermoplastic elastomer material that is suitable for protecting and insulating integrated circuits and integrated circuit components and for use in contact with skin tissue during the delivery and administration of electro-stimulation and/or electrotherapy. The preferred material should produce a cleanable, hypoallergenic substrate that is supple and conformable to the skin tissue. The preferred material may also need to be capable of withstanding high temperatures so that the electrode carrier 104 can be boiled or placed in an autoclave to disinfect it. Such materials include, but are not limited to, styrene-ethylene/butylene-styrene (SEBS) polymers.

As FIGS. 6A and 6B illustrate, an antimicrobial agent 604 can be layered on the non-conductive coating 602 (FIG. 6A) or infused within the non-conductive coating 602 (FIG. 6B) to provide an antimicrobial microatmosphere surrounding the skin-penetrating electrodes 110 and other skin-contacting surfaces of the electrode carrier 104. The skin-penetrating electrodes 110 are infused with the antimicrobial agent 604 in either configuration. The antimicrobial agent 604 can retard, control, kill, and/or prevent microbial contamination in addition to or in lieu of the disinfecting/recharging mechanism 106. In FIG. 6A, the top layer of the skin-contacting surfaces imparts the antimicrobial properties of the antimicrobial agent 604, while in FIG. 6B the antimicrobial properties are concentrated in zones of inhibition Z specifically surrounding the skin-penetrating electrodes 110. It is important to concentrate the antimicrobial agent 604 around the skin-penetrating electrodes 110 in the latter configuration because the stop nodules 210 may not be infused with the antimicrobial agent 604. The antimicrobial agent 604 can also be layered on or infused within the surface skin electrodes 112, whether or not they are disposed on the electrode carrier 104 with the skin-penetrating electrodes 110.

Any one or a number of metal ions that have been shown to possess antibiotic activity, including silver, copper, zinc, mercury, tin, lead, bismuth, cadmium, chromium, and thallium ions, may be used in the composition of the antimicrobial agent 604. Preferably, the antimicrobial agent 604 is composed substantially of silver in concentrations that allow the electrodes 110 and 112 to remain conductive without compromising the insulating structures that surround them, such as the stop nodules 210 and non-conductive coating 602, and compromising the pathway of the electrical circuit 108.

As FIG. 7 illustrates, the electrode carrier 104 can also be provided in a two-piece configuration wherein the skin-penetrating electrodes 110 and surface skin electrodes 112 are provided in a disposable interface 700. The disposable interface 700 is formed of a non-conductive material and can be operatively connected to and disconnected from the circuit board 600 such that the skin-contacting surfaces (i.e., the front face of the electrode carrier 104 and the surface skin electrodes 112) and the skin-penetrating surfaces (i.e., the skin-penetrating electrodes 110) of the electrode carrier 104 can easily be removed from the circuit board 600 for disinfecting and/or replacement. Providing a disposable interface 700 provides an alternative or additional safety measure for protecting the electronic components on the circuit board 600 from damage during disinfecting operations, such as boiling or autoclaving. It also allows the skin-contacting surfaces and skin-penetrating surfaces of the electrode carrier 104 to be commercially replaceable without also requiring replacement of the circuit board 600 or any of its associated components.

As FIGS. 7-10 illustrate, each skin-penetrating electrode 110 within the disposable interface 700 may be electrically coupled to the circuit board 600 via a corresponding first electrical coupling 702 disposed on the circuit board 600. Accordingly, the circuit board 600 includes an array of first electrical couplings 702 disposed thereon in a rectangular array that is also defined by columns V and rows H so that each skin-penetrating electrode 110 independently matches up with its corresponding first electrical coupling 702 when the disposable interface 700 is disposed on the circuit board 600. Similarly, when the surface skin electrodes 112 are also provided in the disposable interface 700, the circuit board 600 also includes an array of second electrical couplings 800 defined by columns V' and rows H' so that each surface skin electrode 112 independently matches up with its corresponding second electrical coupling 800 when the disposable interface 700 is disposed on the circuit board 600. The skin-penetrating electrodes 110 illustrated in FIG. 7 are disposed on the crest sections 506 of an electrode carrier 104 (e.g., FIG. 5) rather than in stop nodules 210 (e.g., FIG. 4), but the disposable interface 700 may be constructed in either configuration.

The disposable interface 700 may also be constructed with the surface skin electrodes 112 disposed on the circuit board 600 rather than on the disposable interface 700. In that configuration, the disposable interface 700 will include openings (not shown) defined by columns V' and rows H' that align with the surface skin electrodes 112 on the circuit board 600 so that the surface skin electrodes 112 can make electrical contact with a patient's skin when the disposable interface 700 is disposed on the circuit board 600. Also in that configuration, the surface skin electrodes 112 may be anchored to the circuit board 600 by any suitable technique, such as soldering. And, as yet another alternative, the surface skin electrodes 112 may be adhesively attached to the front face of the disposable interface 700 between the rows of skin-penetrating electrodes 110 so they can be adhered to and subsequently peeled off of the disposable interface 700 so as to allow more freedom in the configuration of the first electrical couplings 702 and their associated electrical connections 802 on the circuit board 600. That configuration also allows the various components of an electrode carrier 104 to be subjected to certain disinfecting operations, such as boiling or autoclaving, after peeling off the surface skin electrodes 112 when all of the other components of the electrode carrier 104 (e.g., the skin-penetrating electrodes, the circuit board 600, and the non-conductive coating 602) are configured to be subjected to that disinfecting procedure and the surface skin electrodes 112 are not. There may be circumstances when it is more economical to make certain portions of the electrode carrier 104 disposable and others not.

To place the skin-penetrating electrodes 110 and the surface skin electrodes 112 in electrical communication with the pulse generator 102, the first electrical couplings 702 and second electrical couplings 800 are electrically connected to the pulse generator 102 via independent electrical connections 802 and 804, respectively, so as to separately connect each independent electrode 110 and 112 to a separate channel of the pulse generator 102. In the alternative, the skin-penetrating electrodes 110 and the surface skin electrodes 112 can be configured such that each skin-penetrating electrode 110 is coupled in series to an adjacent skin-penetrating electrode 110 in the same row H and such that each surface skin electrode 112 is coupled in series to an adjacent surface skin electrode 112 in the same row H' (e.g., FIG. 9). And, as yet another alternative, the skin-penetrating electrodes 110 and the surface skin electrodes 112 can be configured such that each skin-penetrating electrode 110 is coupled in series to an adjacent skin-penetrating electrode 110 in the same column V and such that each surface skin electrode 112 is coupled in series to an adjacent surface skin electrode 112 in the same column V' (e.g., FIG. 10). Coupling the rows H and H' or columns V and V' as described reduces the number of channels required by the pulse generator 102 to operate the electrodes 110 and 112, with one channel corresponding to each row H and H' or column V and V'.

Each independent electrical coupling 702 and 800 on the circuit board 600 is connected to the pulse generator 102 via a single, bundled electrode cable 206 comprising an insulated wire for each channel of the pulse generator 102 used to apply electro-stimulation. An attachment mechanism 806, such as an interlocking fabric or double stick tape with peel-away backing, may be disposed between the skin-penetrating electrodes 110 and/or the surface skin electrodes 112 to removably attach the disposable interface 700 to the circuit board 600 so the disposable interface 700 can be placed on and subsequently peeled off of the circuit board 600. The disposable interface 700 also may be attached to the circuit board 600 via a mechanical connection, such as clips or clamps. And, when the skin-penetrating electrodes 110 are disposed on the crest sections 506 of the disposable interface 700, they may be configured to include circular portions 704 (FIG. 7) for providing additional contact area when electrically coupling the skin-penetrating electrodes 110 to their respective first electrical couplings 702.

As FIGS. 11 and 12 illustrate, a non-conductive adhesive strip 1100 may be applied in the valley sections 504 of the electrode carrier 104 illustrated in FIG. 5 to assist in adhesive fixation of the surface skin electrodes 112 and the electrode carrier 104 to a patient's skin tissue during treatment use. Non-conductive adhesive strips 1100 may also be disposed along the outside edge of the electrode carrier 104 to provide additional adhesion (not shown). And, the adhesive strips may also be disposed between the skin-penetrating electrodes 110 and the surface skin electrodes 112 in a pattern similar to that of the attachment mechanism 806 illustrated in FIGS. 8-10. In each of those configurations, the non-conductive adhesive strips 1100 must be arranged so they do not cover the surface skin electrodes 112 and/or interfere with the transfer of electric stimulation to a patient's skin via the surface skin electrodes 112. Instead, the surface skin electrodes 112 should be covered with electrically conductive gel or hydrogel or any conventional coupling medium (e.g., a non-conductive adhesive through which current can pass substantially unobstructed) for enhancing uniform conductivity at the electrode-skin interface, and for increasing surface area conductivity. The coupling medium may also be used to electrically couple adjacent surface skin electrodes 112 with one another across the front face of the electrode carrier 104.

Both the disposable interface 700 and the circuit board 600 may include a plurality of venting bores 1200, illustrated as square holes in FIG. 12, that put a patient's skin at the front face of the electrode carrier 104 in fluid communication with the atmosphere at the rear face of the electrode carrier 104 so as to ventilate moisture and perspiration that may be released from the patient's skin while the electrode carrier 104 is disposed thereon—particularly while the patient is receiving electro-stimulation and/or electrotherapy. To facilitate ventilation through both the disposable interface 700 and the circuit board 600, the venting bores 1200 in the disposable interface 700 are configured to align with corresponding venting bores 1200 in the circuit board 600 when the disposable interface 700 is attached to the circuit board 600. That alignment allows moisture and perspiration that is released from a patient's skin while the electrode carrier 104 is disposed on the patient's skin to escape properly through the venting bores 1200. In a one-piece electrode carrier 104 (e.g., FIGS. 6A and 6B), the venting bores 1200 merely extend all of the way through the electrode carrier 104.

A wearable applicator (not shown), such as a garment fitted for a particular body segment, strap, belt, bandage, splint, stabilizer, supporter, brace or cast may be used to assist in the proper positioning and placement of the electrode carrier 104 and electrodes 110 and 112. Fasteners, including interlocking fabrics, buttons, snaps, zippers, and the like can be used to join the electrode carrier 104 with the wearable applicator such that the electrode carrier 104 can be anatomically positioned for therapeutic effectiveness on a wide range of body parts.

Disinfecting/Recharging Mechanism 106

The disinfecting/recharging mechanism 106 reduces microbial reproduction on the skin-penetrating surfaces of the skin-penetrating electrodes 110 and the skin-contacting surfaces of the electrode carrier 104 and surface skin electrodes 112 by applying germicidal radiation to those surfaces for a sufficient time and strength to inactivate common skin pathogens, including bacteria spores, molds, protozoa, viruses and yeast. In a preferred embodiment, the disinfecting/recharging mechanism 106 uses germicidal ultraviolet light to damage the pathogens' genetic material, thereby inhibiting the pathogens' replication and colony formation. The required dose to inactivate 90% of most types of infection-causing microbes is within a range of about 2 to 6 $mJ/cm^2$. Dosages of UV intensity of about 500 to 1500 $\mu W/cm^2$ for up to about one hour of exposure time can be sufficient to inactivate the microbes by damaging their DNA, and can even destroy the microbes by disrupting their cellular processes. Accordingly, the disinfecting/recharging mechanism 106 is configured to apply germicidal radiation up to approximately 1000 $J/cm^2$ for several sessions per day (in between electro-stimulation treatment uses) over periods of an hour or more.

Figure 13:
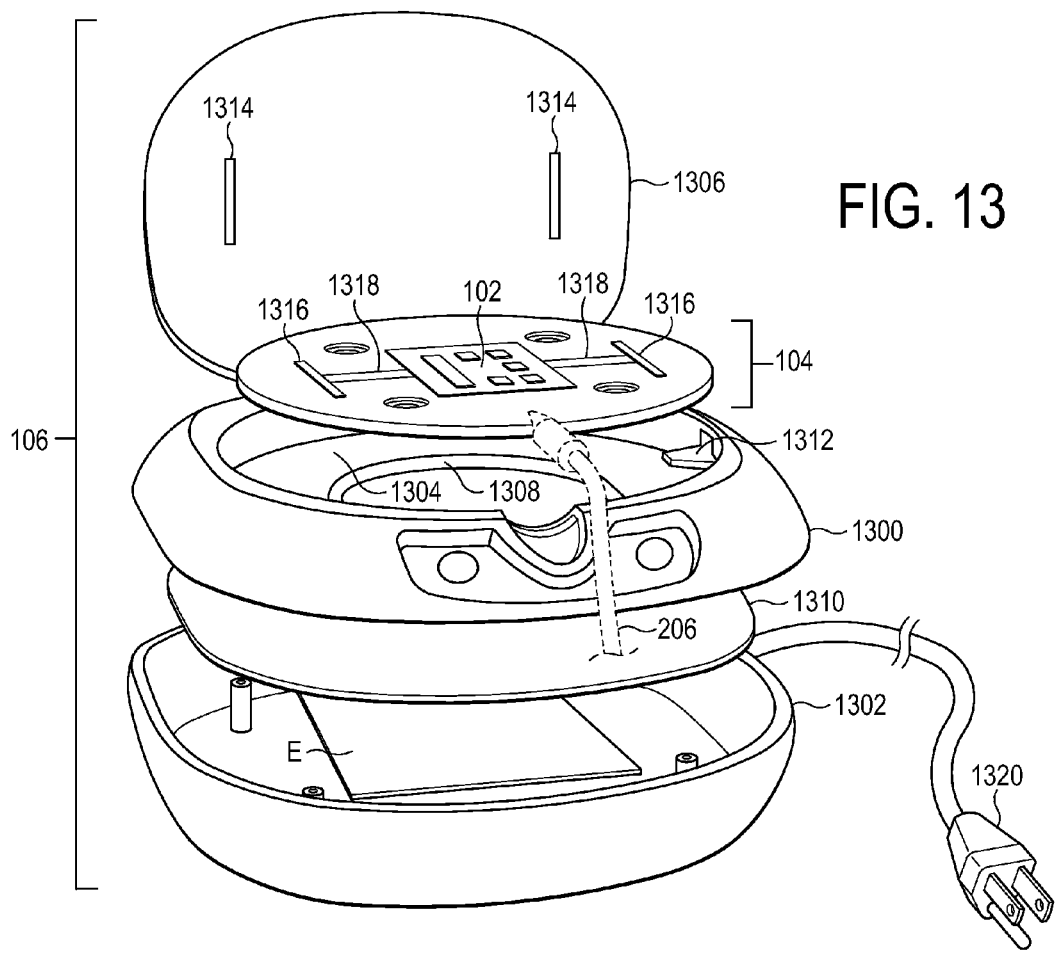
FIG. 13 is an isometric view of an electrotherapy system in accordance with a non-limiting embodiment of the present invention.

As FIG. 13 illustrates, the disinfecting/recharging mechanism 106 includes an upper casing 1300 and a lower casing 1302 that form a disinfecting chamber 1304 therein that can be closed off with a UV absorbent lid 1306. A UV Lamp 1308 is disposed in the disinfecting chamber 1304 applying germicidal ultraviolet light. The disinfecting chamber 1304 is suitably sized and dimensioned to position the skin-penetrating surfaces of the skin-penetrating electrodes 110 and the skin-contacting surfaces of the electrode carrier 104 and surface skin electrodes 112 at an appropriate distance from the UV lamp 1308 to apply the required amount germicidal ultraviolet light to disinfect those surfaces. For example, the disinfecting chamber 1304 may be sized and dimensioned so that the skin-penetrating surfaces of the skin-penetrating electrodes 110 are at a distance of approximately 1 to 5 cm from the UV lamp 1308 when the array of skin-penetrating electrodes 110 is positioned within the chamber 1304 with the front face (i.e., the side placed against a patient's skin) down so the skin-penetrating electrodes 110 extend toward the UV lamp 1308. In FIG. 13, the electrode carrier 104 is illustrated with its front face facing downward and away from the vantage point from which FIG. 13 was taken so that the skin-penetrating electrodes 110 and the surface skin electrodes 112 are not visible. Instead, only the rear face (i.e., the side facing away from a patient's skin) of the electrode carrier 104 is shown.

A reflector 1310 may disposed between the upper casing 1300 and lower casing 1302 of the disinfecting/recharging mechanism 108 to provide the floor and surrounding surfaces of the chamber 1304. The reflector 1310 may be made of aluminum or may have an aluminum surface. The reflector 1310 and its reflective surface may be made of any suitable material known for producing a relatively high reflectivity index for ultraviolet radiation.

The disinfecting chamber 1304 may also include any suitable number of platforms 1312 (shown and hidden) to properly support and position the electrode carrier 104 in the disinfecting/recharging mechanism 106. The platforms 1312 should be positioned, sized, and dimensioned such that there is minimum interference with the skin-penetrating electrodes' 110 exposure to the germicidal radiation.

Different configurations of the chamber 1304 and UV lamp 1308 may also be used. For example, the UV lamp 1308 may be positioned above the skin-penetrating electrodes 110 to emit the radiation in a downward direction. In that configuration, the skin-penetrating electrodes 110 are positioned within the chamber 1304 on a sliding tray (not shown) with the front face up, wherein the sliding tray is used to slide the electrode carrier 104 in and out of the chamber 1304. The chamber 1304 may also be constructed and configured to allow electrode carriers 104 of different shapes and sizes (e.g., FIGS. 4 and 5), and/or more than one electrode carrier 104 at a time, to be irradiated and/or recharged in the disinfecting/recharging mechanism 106.

The UV lamp 1308 may be any shaped or non-shaped commercially available germ-killing lamp configured to generate radiation in the required UV range. The UV lamp's 1308 shape may be dependent upon the size and shape of the electrode carrier 104 and the chamber 1304 needed to enclose the electrode carrier 104. In a preferred embodiment, the UV lamp 1308 is a low pressure mercury vapor lamp having a U-shape that is configured to be an upside-down U when positioned in the chamber 1304, but any suitable commercially available UV lamp having a Wattage of approximately 2-6 Watts or more and that is configured to deliver germicidal radiation may be used. The wavelength of the electromagnetic radiation delivered by the UV lamp 1308 is in the range of about 240 to 280 nanometers, preferable about 254 nanometers. A medium or high pressure mercury vapor lamp, LED, or laser capable of generating the preferred 254 nanometers and other known bands of germicidal light may also be used. And, more than one lamp and/or type of lamp may be used in combination.

In addition to or as an alternative to using germicidal ultraviolet light to disinfect the electrode carrier 104, boiling water and/or steam may also be used to disinfect the electrode plate 104. Accordingly, the disinfecting/recharging mechanism 106 may be configured with components for introducing boiling water and/or steam into the chamber 1304. In that configuration, the upper casing 1300 and the lid 1306 may include sealing surfaces (not shown) to maintain a seal to withstand the high pressures associated with autoclaving medical devices. The disinfecting/recharging mechanism 106 may also be configured to use any other suitable disinfecting mechanism.

The disinfecting aspect of the disinfecting/recharging mechanism 106 is intended to enhance the electrotherapy system's 100 outpatient reusability. More particularly, by providing such disinfecting functionality, the methods and devices of the present invention can be employed with portability for outpatient treatment in a manner prescribed by a physician. And, although the electrotherapy system 100 is not intended to be shared from patient to patient, the disinfecting/recharging mechanism 106 will also minimize the risk of disease transmission from one patient to another, while minimizing the risk from environmental sources to a patient, should it be used in that manner.

In addition to the disinfecting function, the disinfecting/recharging mechanism 106 may serve as a recharging station. Accordingly, the disinfecting/recharging mechanism 106 illustrated in FIG. 13 includes a pair of recharging conductors 1314 configured to mate with a corresponding pair of recharging conductors 1316 on the electrode carrier 104 for recharging the power source 114 (FIG. 1) of the pulse generator 102. As illustrated in FIG. 13, the pulse generator 102 is disposed on the electrode carrier 104 rather than in an electrically connected but physically separate device, as illustrated in FIG. 2. The pulse generator 102 is connected to the recharging conductors 1316 via electrical connections 1318. The conductors 1316 and electrical connections 1318 are disposed on the rear face of the electrode carrier 104 to allow electrical communication with the conductors 1314 on the disinfecting/recharging mechanism's 106 lid 1306 so the pulse generator 102 can be electrically coupled to the disinfecting/recharging mechanism 106 for recharging during periods of non-use.

Other configurations of conductors 1316 and electrical connections 1318 may also be used depending on the size and shape of the electrode carrier 104 and disinfecting/recharging mechanism 106, as well as the type and recharging load of the system's 100 power source 114 (FIG. 1). In addition, a separate (i.e., not incorporated into the disinfecting/recharging mechanism 106) battery charging station may be used in addition to the disinfecting/recharging mechanism 106. And, when the pulse generator 102 is electrically connected to but physically separate from the electrode carrier 104, as illustrated in FIG. 2, the disinfecting/recharging mechanism 106 may be configured to accommodate the electrode cable 208 (dotted-line) that provides electrical communication between the pulse generator 102 and the electrode carrier 104.

The electronics for the disinfecting/recharging mechanism 106 are represented by "E" and may be housed in the lower casing 1302 of the disinfecting/recharging mechanism 106. The disinfecting/recharging mechanism 106 may have a number of electronic features, including the display of outputs for apprising a patient of the percentage that the disinfection and/or recharging functions are complete. The disinfecting/recharging mechanism 106 may also have a separate indicator or plurality of indicators that display when the disinfection function and/or the recharging function are completed. The disinfecting/recharging mechanism 106 may receive power for each of its functionalities via a conventional outlet plug 1320 or any other suitable power source.

Electrotherapy

The electrotherapy system 100 of the present invention provides temporary relief from the symptoms of chronic pain by targeting cutaneous thin Aδ and C nerve fibers while stimulating Aβ nerve fibers to help mask the aversive feeling from the Aδ and C nerve fiber stimulation. For example, the use of TENS to target Aβ nerve fibers can be combined with CFS to help reduce and mask the aversive feeling from the Aδ and C nerve fiber stimulation of CFS. The combination of TENS with CFS is based on the body's response to different types of pain. Electrical impulses in response to acute pain sensations are transmitted to the brain through peripheral nerves and the spinal cord. At the time point of an injury, the signal is transmitted by nociceptive primary afferent nerve fibers to the dorsal horn of the spinal cord. Nociceptive primary afferent neurons belong to the Aδ and C nerve fibers. At the dorsal horn and in the spinal cord or its trigeminal analogue, secondary neurons take over by transferring the signal to the thalamus and finally to the cerebral cortex. Input in tactile Aβ nerve fibers is known to interact with cutaneous nociceptive-input in the spinal cord and higher centers causing relief of pain. Therefore, by targeting the Aβ nerve fibers via the use of TENS, the aversive sensation caused by stimulation of the Aδ and C nerve fibers via CFS can be masked, resulting in more tolerable electrotherapy to assist in the symptomatic relief of chronic pain.

The electrotherapy system 100 also provides an effective alternative to known treatments of localized histamine-induced itching in a similar manner. Accordingly, the surface skin electrodes 112 are configured to apply electro-stimulation to Aβ nerve fibers and the skin-penetrating electrodes 110 are configured to apply electro-stimulation to Aδ and C nerve fibers. The pulse generator is configured to transmit pulsed currents into a patients skin via the skin-penetrating electrodes 110 and the surface skin electrodes 112.

Figure 14:
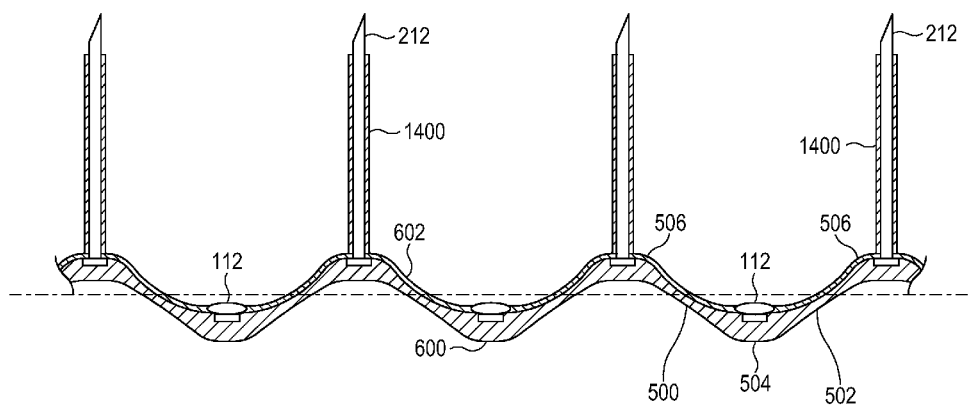
FIG. 14 is a side view taken in section of skin-penetrating and surface skin electrodes prior to being applied to a patient's skin.
Figure 15:
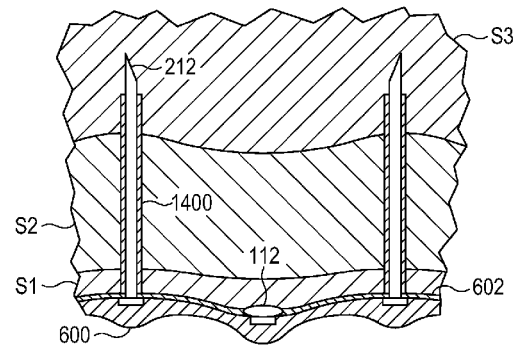
FIG. 15 is a side view taken in section of skin-penetrating and surface skin electrodes applied to a patient's skin.

FIGS. 14 and 15 illustrate skin-penetrating electrodes 110 and surface skin electrodes 112 before and during application to a patient's skin tissue, respectively. The elements illustrated in those figures are exaggerated for clarity. As FIG. 14 illustrates, the electrode carrier 104 includes valley sections 504 and crest sections 506 formed by rounded side walls 500 and 502. The skin-penetrating portions 212 of the skin-penetrating electrodes 110 extend from the crest sections 506 and are insulated with an insulating material 1400 along the length of the skin-penetrating portion 212 so that the amount of "active" length exposed to the patient's dermis S3 has a sufficiently small surface area to provide the high electrical current density required to activate and recruit Aδ and C nerve fibers. There may also be instances where the skin-penetrating portions 212 need not extend all the way into the dermis S3 to activate and recruit Aδ and C nerve fibers. But, in no case will the skin-penetrating portions 212 need to extend any deeper than the dermis S3.

As FIG. 15 illustrates, the non-conductive coating 602 of the electrode carrier 104 abuts the stratum corneum S1 (i.e., the top layer of the epidermis S2) of the skin tissue when the electrode carrier 104 is applied to a patient's skin. In that position, the skin-penetrating portions 212 of the skin-penetrating electrodes 110 penetrate and extend through the stratum corneum S1 and the epidermis S2 into the dermis S3, where the active portion can target the Aδ and C nerve fibers. The valley sections 504 are also compressed so that the surface skin electrodes 112 are placed in contact with the stratum corneum S1 of the epidermis S2, where they can transcutaneously target Aβ nerve fibers.

With the skin-penetrating electrodes 110 and the surface skin electrodes 112 properly disposed on a patient's skin as illustrated in FIG. 15, electro-stimulation can be produced through any of the skin-penetrating electrodes 110 and/or surface skin electrodes 112. Preferably, one or more surface skin electrode(s) 112 is used as a collector electrode for the skin-penetrating electrodes 110 and/or the surface skin electrodes 112 that are producing electro-stimulation. To avoid current always passing through the same surface skin electrode 112 when electro-stimulation is applied via the surface skin electrodes 112, the pulse generator 102 may be programmed to alternate between the surface skin electrodes 112 through which electro-stimulation is being applied, including alternating which surface skin electrode(s) 112 is being used as a collector electrode. If no electro-stimulation is being applied via the surface skin electrodes 112, all of the surface skin electrodes 112 may be used as collector electrode for the electro-stimulation being applied through the skin-penetrating electrodes 110.

Electro-stimulation may be applied via a surface skin electrode 112 that is phase locked with the electro-stimulation applied via a neighboring skin-penetrating electrode 110. The electro-stimulation applied via the surface skin electrodes 112 generates signals produced in Aβ nerve fibers and the electro-stimulation applied via the skin-penetrating electrodes 110 generates signals produced in the Aδ and C nerve fibers. The two types of electro-stimulation are phase locked so that the signals produced in Aβ nerve fibers will arrive at the patient's spinal cord prior to and/or overlapping in time with the signals produced in the Aδ and C nerve fibers.

Pairs and/or other combinations of skin-penetrating electrodes 110 and surface skin electrodes 112 can be activated consecutively in either a random or orderly pattern. For example, a random, non-consecutive pattern of electro-stimulation can be applied by alternately activating one or more column V' or row H' of surface skin electrodes 112 prior to and/or overlapping in time with a random skin-penetrating electrode 110 or with a combination of skin-penetrating electrodes 110. And, an orderly, consecutive pattern of electro-stimulation can be applied by consecutively activating phase locked pairs of surface skin electrodes 112 and skin-penetrating electrodes 110 in a sequence starting at one side (i.e., an edge) of the electrode carrier 104 and proceeding to the other side of the electrode carrier 104.

The non-consecutive pattern of electro-stimulation creates a sensation of massaging stimulation that is therapeutically effective in providing electroanalgesia for the treatment of pain. And, the consecutive pattern of electro-stimulation creates a sensation of a sweeping stimulation that mimics the sequence of stimulation that occurs naturally when scratching or massaging the skin, which is particularly useful in treating patients suffering from chronic pain or itch. Both of those patterns can be achieved with a configuration of skin-penetrating electrodes 110 and surface skin electrodes 112 such as that provided for in FIG. 8, wherein each of the skin-penetrating electrodes 110 and surface skin electrodes 112 has a separate electrical coupling 800 and 702, respectively, such that a different channel of the pulse generator 102 can be used to separately control each skin-penetrating electrode 110 and each surface skin electrode 112.

Figure 9:
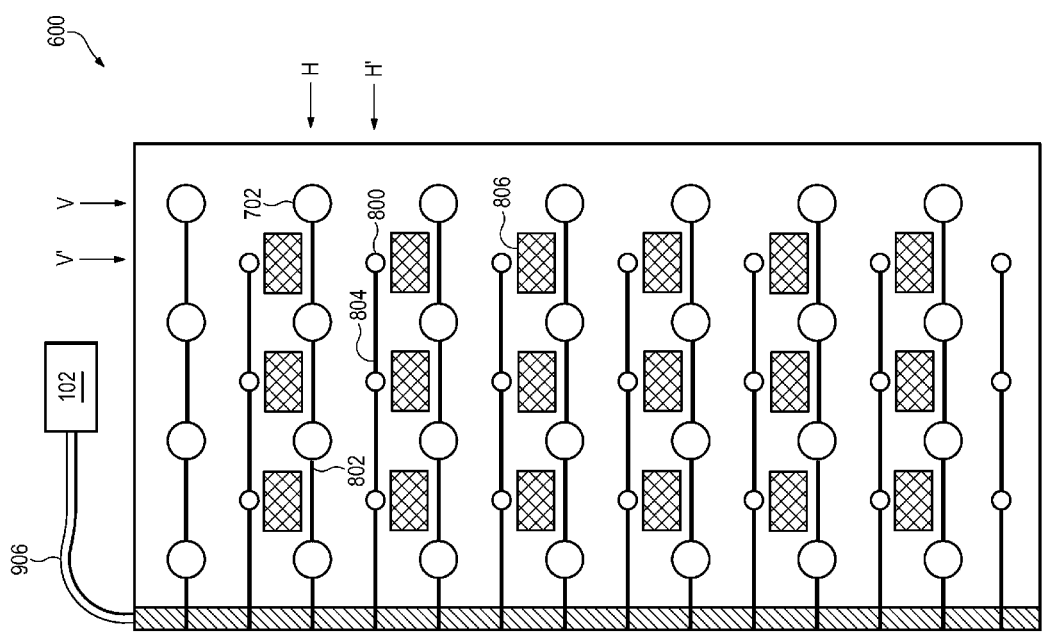
FIG. 9 is a plan view of the front face of another embodiment of the circuit board of FIG. 5.
Figure 10:
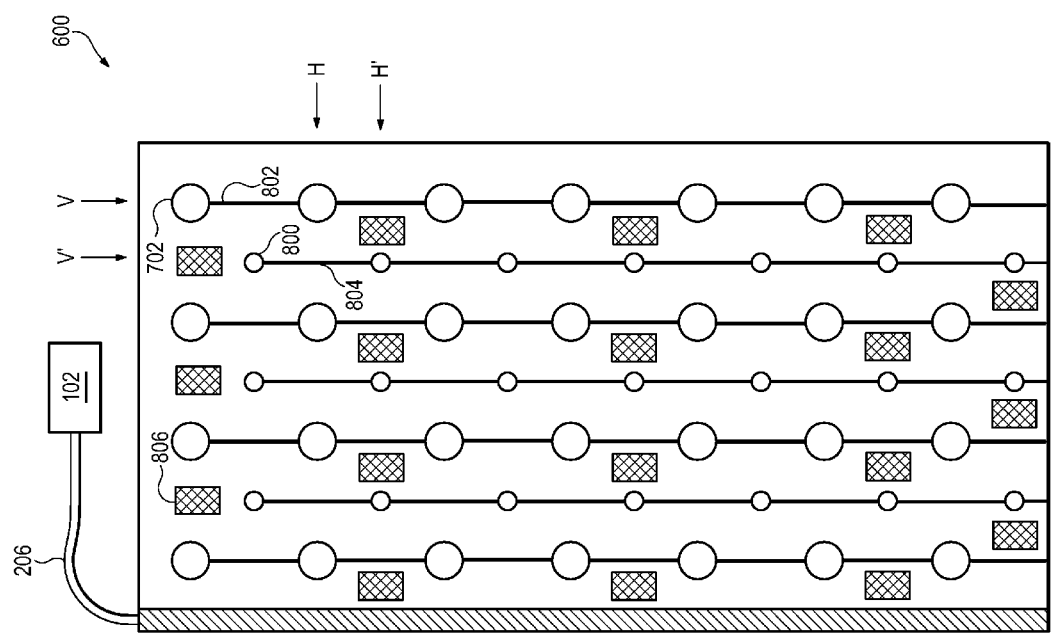
FIG. 10 is a plan view of the front face of yet another embodiment of the circuit board of FIG. 5.

Non-consecutive and consecutive patterns of electro-stimulation may also be achieved with a configuration of skin-penetrating electrodes 110 and surface skin electrodes 112 such as that provided for in FIG. 9 or 10, wherein the skin-penetrating electrodes 110 and the surface skin electrodes 112 are connected in series into separate rows H and H' or columns V and V', respectively. The non-consecutive pattern of electro-stimulation can be applied by alternately activating one or more column V' or row H' of surface skin electrodes 112 prior to and/or overlapping in time with a random column V or row H of skin-penetrating electrodes 110. And, the consecutive pattern of electro-stimulation can be applied by consecutively activating paired columns V and V' or rows H and H' of skin-penetrating electrodes 110 and surface skin electrodes 112 in a sequence starting at one side of the electrode carrier 104 and proceeding to the other side of the electrode carrier 104.

The surface skin electrode 112 can be used to target Aβ nerve fibers within a patient's skin tissue using a biphasic pulsed current comprising pulse trains with pulse durations $T_1$ of about 0.05 to 0.30 milliseconds and a pulse string frequency of about 50 to 400 Hertz. The biphasic pulsed current may be applied in a continuous pulse string within a predefined period (e.g., 100 pulses of 0.25 millisecond duration applied over 1000 milliseconds at a continuous frequency of 100 Hz) or broken up into bursts of pulses over a predefined period. When applied as bursts of pulses, the biphasic pulsed current has a burst duration of up to about 100 milliseconds and a burst frequency of about 0.1 to 10 Hertz. The biphasic pulsed current has a current amplitude of up to about 50 milliamperes. The waveform of the biphasic pulsed current used to target Aβ nerve fibers may be either symmetric or asymmetric.

Figure 16:
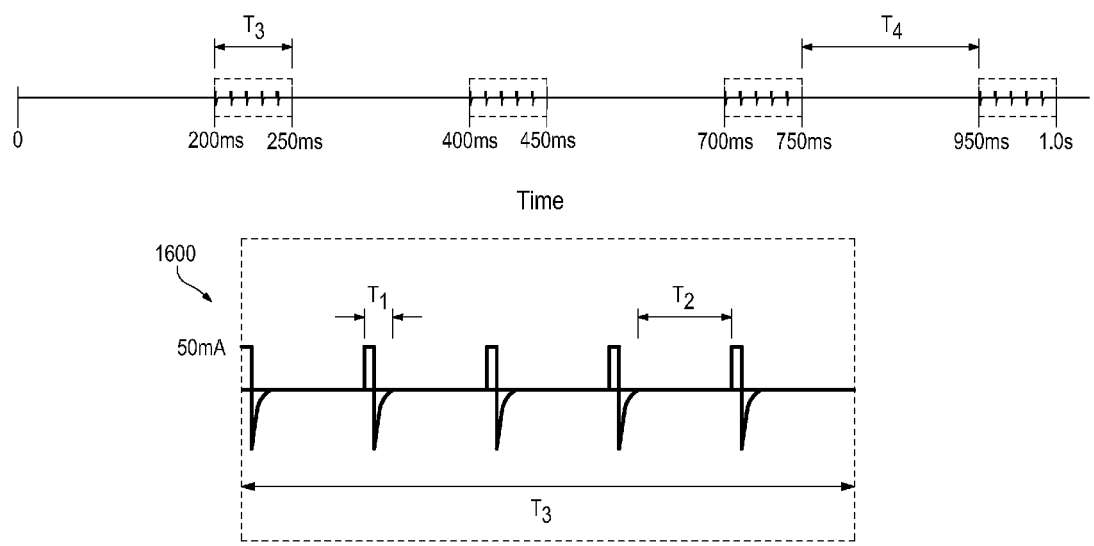
FIG. 16 is a graph illustrating the waveform of a train of pulse bursts of biphasic pulsed current in accordance with a non-limiting embodiment of the present invention.

FIG. 16 illustrates an exemplary asymmetric biphasic waveform 1600 that can be used by the present invention to target Aβ nerve fibers via the surface skin electrodes 112. That biphasic waveform 1600 has a period of one second and generates a current with a pulse duration $T_1$ of 0.15 milliseconds and an interpulse interval $T_2$ of 9.85 milliseconds that form pulse bursts having a burst duration $T_3$ of 50 milliseconds and an interburst interval $T_4$ of 200 milliseconds. The intraburst, or pulse string frequency within the burst, is 100 Hertz (i.e., 100 pulses of 10 millisecond duration per second), and the burst frequency is 4 Hertz (i.e., 4 bursts of 250 millisecond duration per second).

The skin-penetrating electrodes 110 can be used to target Aδ and C nerve fibers within a patient's skin tissue using a monophasic pulsed current comprising continuous pulse trains with pulse durations $T_1$ of about 0.5 to 10.0 milliseconds, a pulse string frequency of about 0.1 to 10 Hertz, and a current amplitude of up to about 2 milliamperes. The longer pulse durations $T_1$ are useful for the recruitment of C nerve fibers. And, by staggering the monophasic pulsed current across different skin-penetrating electrodes 110, the overall frequency of stimulation can be increased over the field of stimulation. For example, if the monophasic pulsed current has a frequency of 4 Hz, an electrotherapy system 100 having fourteen (14) skin-penetrating electrodes can apply electro-stimulation with a frequency of approximately 56 Hertz (i.e., 14 electrodes×4 Hz=56 Hz).

Figure 17:
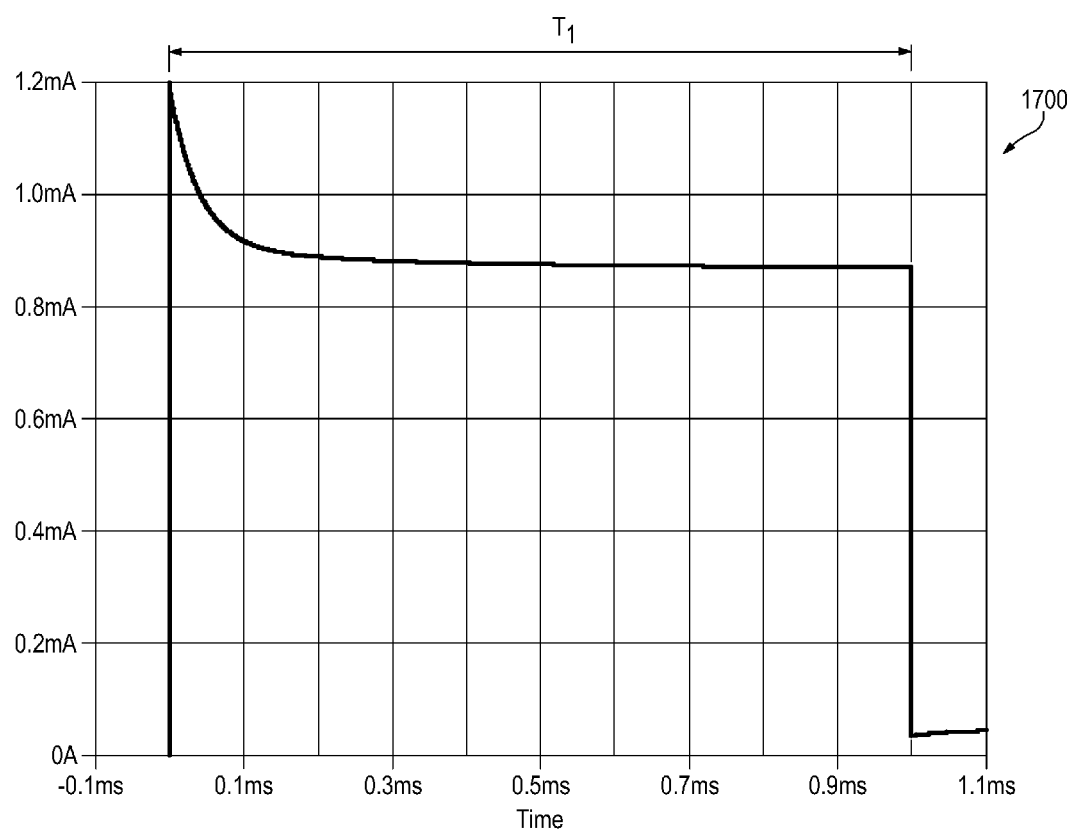
FIG. 17 is a graph illustrating the waveform of a single monophasic pulse of electrical current in accordance with a non-limiting embodiment of the present invention.

FIG. 17 illustrates an exemplary waveform 1700 of an individual monophasic pulse that can be used by the present invention to target Aδ and C nerve fibers within a patient's skin tissue via the skin-penetrating electrodes 110. The characteristics of the pulse conditioning circuit 128 in the return electrical pathway between the skin-penetrating electrodes 110 and surface skin electrodes 112 cause the waveform 1700 of that pulse to approximate a rectangular wave. That waveform 1700 has a pulse duration $T_1$ of 1.0 millisecond and a current amplitude varying from about 0.8 to 1.2 milliamperes from the pulse onset. The current amplitude is at its maximum value for less than 0.1 milliseconds after the pulse onset. Preferably, the maximum current amplitude will be about 0.5 to 2 milliamperes and will last a maximum of about 0.25 milliseconds after the pulse onset. The maximum current amplitude can then be reduced by about 5 to 50 percent for the remainder of the pulse duration. The current amplitude in milliamperes is measured as a function of time in milliseconds.

Figure 18:
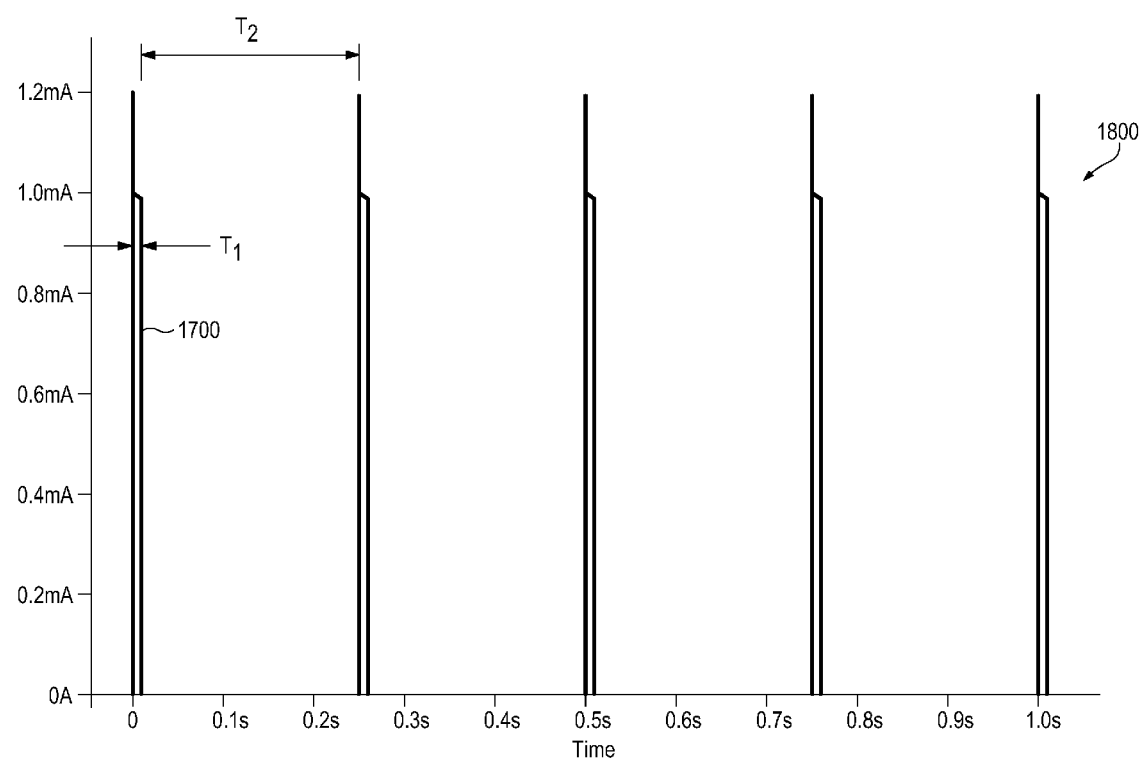
FIG. 18 is a graph illustrating the waveform of a pulse train of monophasic pulsed current made up of a plurality of the pulses of FIG. 18.

FIG. 18 illustrates an exemplary waveform 1800 of a train of the monophasic pulses illustrated in FIG. 17 with a period of one second. The pulse duration $T_1$ is 1.0 milliseconds, the interpulse interval $T_2$ is 249 milliseconds, and the frequency is about 4 Hertz (i.e., 4 pulses per second). Accordingly, the monophasic pulsed current is applied as a continuous pulse string rather than in pulse bursts.

Figure 19:
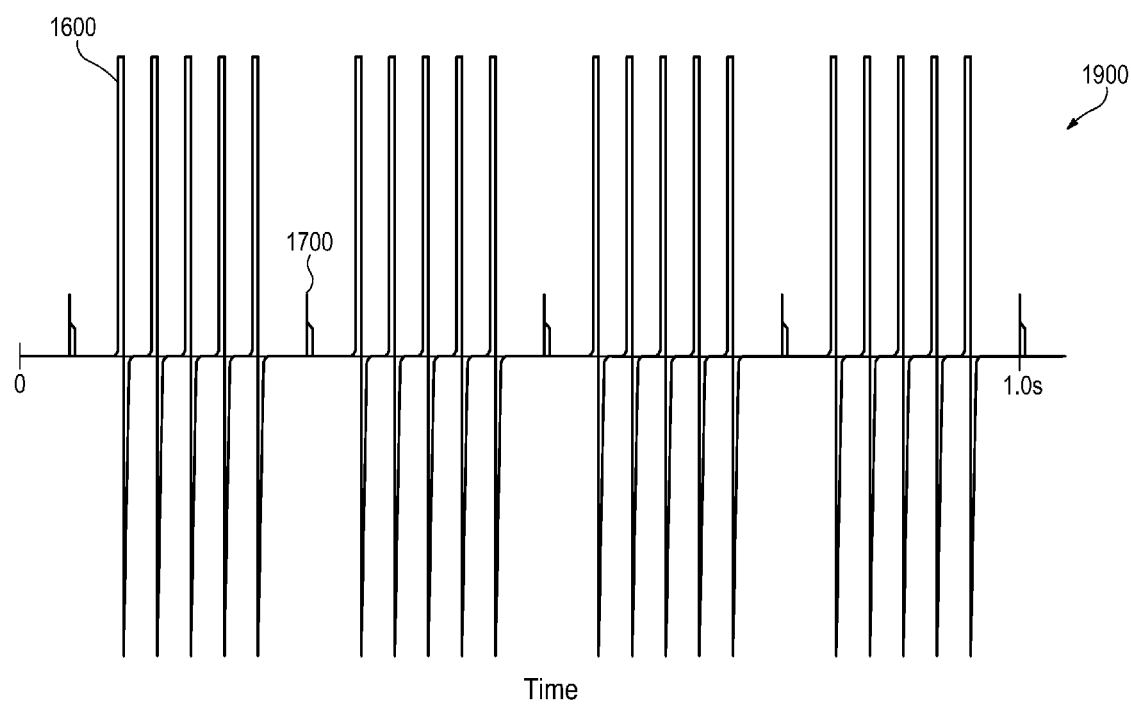
FIG. 19 is a graph illustrating the waveform of a combination of the waveform of FIG. 16 and the waveform of FIG. 18 in accordance with a non-limiting embodiment of the present invention.

FIG. 19 illustrates an embodiment of a waveform 1900 of current that can be driven through a patient's skin by the electrotherapy system 100 using a combination of the asymmetric biphasic waveform 1600 applied by the surface skin electrodes 112 and the train of monophasic approximate square waveforms 1800 applied by the skin-penetrating electrodes 110. As illustrated, the waveforms 1600 and 1800 are applied so that the individual monophasic pulses 1700 generated with the skin-penetrating electrodes 110 occur alternatively in time between the asymmetric biphasic waveform 1600 generated with the surface skin electrodes 112. In the alternative, the individual monophasic pulses 1700 generated with the skin-penetrating electrodes 110 may be applied so as to overlap in time with the asymmetric biphasic waveform 1600 generated with the surface skin electrodes 112, or the asymmetric biphasic waveform 1600 generated with the surface skin electrodes 112 can occur prior in time (and/or subsequent in time) to the monophasic approximate square waveforms 1800 generated with the skin-penetrating electrodes 110. Each of those different combinations of waveforms 1600 and 1800, and iterations thereof, may also be used in combination with each other. The illustrated waveforms 1600, 1800, and 1900 are not to scale, with the size of the individual monophasic pulses 1700 being exaggerated for clarity.

Accordingly, a combination of waveforms 1600 and 1800 that more similar to the waveform 1900 illustrated in FIG. 19 may be required to ensure that the waveforms 1600 and 1800 from the surface skin electrodes 112 and skin-penetrating electrodes 110, respectively, arrive at the patient's spinal cord at the same time and produce the desired masking effect.

During a treatment session, a patient can use the pulse generator 102 to begin applying the asymmetric biphasic waveform 1600 with the surface skin electrodes 112. While applying the asymmetric biphasic waveform 1600 with the surface skin electrodes 112, the patient can then gradually begin applying the monophasic approximate square waveforms 1800 with the skin-penetrating electrodes 110. The patient can increase the stimulation applied with the skin-penetrating electrodes 110 in gradual steps during the first minutes of a treatment session using the toggle keys 200 on the pulse generator, which allows the patient to adapt to the signals produced by those pulsed currents to a comfortable level as treatment is applied. Ultimately, that allows the patient to achieve a much higher level of comfortable Aδ and C nerve fiber stimulation with the skin-penetrating electrodes 110 than the patient could otherwise comfortably achieve. And, the relative strength of the Aβ nerve fiber stimulation with the surface skin electrodes 112 may be reduced over time as the patient adapts to the sensation of the Aδ and C nerve fiber stimulation. In addition, as the patient continues with subsequent sessions of therapy, the relative strength of the Aβ nerve fiber stimulation can be varied (reduced or increased) depending on the patient's adaptation to the Aδ and C nerve fiber stimulation.

After a treatment session using one of the disclosed methods, a patient can easily disinfect or cheaply dispose of the skin-contacting and skin-penetrating portions of the electrotherapy system 100. The electrode carrier 104 can be disinfected for reuse by the patient by placing it in the disinfecting/recharging mechanism 106. The patient can further minimize the risk of environmental contaminants by using commercially available detergents, disinfectants, and other non-residue cleaners to dampen the skin-contacting and skin-penetrating surfaces of the electrode carrier 104. The surface of each skin-penetrating electrode 110 can then be agitated and swabbed and, finally, wiped clean with commercially available antiseptic wipes and isopropyl alcohol. After the cleaned surfaces are dried, the electrode carrier 104 and/or disposable interface 700 may be stored in the disinfecting/recharging mechanism 106 until the next treatment session. In the alternative, the patient can remove and discard the disposable interface 700 and replace it with a new, sterilized disposable interface 700 that is commercially available.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An electrotherapy system for stimulating sensory nerves within skin tissue, said system comprising:
   an electrode carrier having an external non-conductive coating;
   a pulse generator electrically connected to said electrode carrier;
   an array of skin-penetrating electrodes disposed on said electrode carrier, each of said skin-penetrating electrodes including a needle-like protrusion;
   at least one surface skin electrode disposed on said electrode carrier, said at least one surface skin electrode being physically spaced and electrically separate from any needle-like protrusions disposed on the electrode carrier; and
   a pulse conditioning circuit operatively connected between said at least one surface skin electrode and said array of skin-penetrating electrodes,
   wherein said pulse generator produces a biphasic pulsed current at said at least one surface skin electrode capable of passing said biphasic pulsed current through the skin tissue; and,
   wherein said pulse generator and said pulse conditioning circuit collectively produce a monophasic pulsed current at each of said skin-penetrating electrodes capable of passing said monophasic pulsed current through the skin tissue.

2. The system of claim 1, wherein said pulse generator provides each of said skin-penetrating electrodes with a pulse train of about 0.1 to 10 Hertz, each pulse in said pulse train characterized by a pulse duration of about 0.5 to 10.0 milliseconds and a current amplitude of up to about 2 milliamperes.

3. The system of claim 2, wherein said current amplitude during a pulse onset reaches a maximum current amplitude of about 0.5 to 2 milliamperes within about 0.25 milliseconds at most from said pulse onset, said maximum current amplitude generated by said pulse conditioning circuit, and wherein said current amplitude is reduced by about 5 to 50 percent thereafter for the remainder of said pulse duration.

4. The system of claim 1, wherein said pulse generator provides said at least one surface skin electrode with pulse trains having a burst frequency of about 0.1 to 10 Hertz, a pulse string frequency within the burst of about 50 to 400 Hertz, a burst duration per each one of said at least one surface skin electrode of up to about 100 milliseconds, a pulse duration of about 0.05 to 0.3 milliseconds, and a current amplitude of up to approximately 50 milliamperes.

5. The system of claim 1, wherein said biphasic and monophasic pulsed currents are configured to administer electroanalgesia at said surface skin electrode and at each of said skin-penetrating electrodes in a non-consecutive pattern of transcutaneous electrical nerve stimulation and skin-penetrating electrical nerve stimulation.

6. The system of claim 1, wherein said pulse conditioning circuit includes at least one of a capacitor in parallel with a resistor, a semiconductor field effect transistor, a digital signal processor, and an inductor.

7. The system of claim 1, wherein each of said skin-penetrating electrodes is configured to target Aδ and C nerve fibers within the skin tissue and said at least one surface skin electrode is configured to target Aβ nerve fibers within the skin tissue.

8. The system of claim 1, wherein said array of skin-penetrating electrodes is removably attached to said electrode carrier and is disposable.

9. The system of claim 1, further comprising:
   an antimicrobial agent infused within or layered upon said array of skin-penetrating electrodes and within or upon said non-conductive coating for reducing microbial reproduction on each of said skin-penetrating electrodes and non-conductive coating.

10. The system of claim 1, further comprising:
    a disinfecting mechanism configured to reduce microbial reproduction on each of said skin-penetrating electrodes and electrode carrier when coupled with said array of skin-penetrating electrodes and said electrode carrier.

11. The system of claim 10, wherein said disinfecting mechanism reduces microbial reproduction with at least one of boiling water and steam.

12. The system of claim 10 further including:
    a rechargeable power source; and
    a recharging mechanism configured to recharge said power source.

13. The system of claim 12 further comprising:
    a housing configured integrally to enclose said disinfecting mechanism and said recharging mechanism.

14. The electrotherapy system of claim 1, wherein
    the electrode carrier is molded around the array of skin-penetrating electrodes; or
    the array of skin-penetrating electrodes is formed separately and removably attached to the electrode carrier.

15. The electrotherapy system of claim 1, wherein
    the at least one surface skin electrode is screen-printed on the electrode carrier; or
    the at least one surface skin electrode is formed separately and removably attached to the electrode carrier.

16. An appliance for electro-stimulating skin tissue, said appliance comprising:
    a printed circuit board (PCB) including an external non-conductive coating;
    at least one surface skin electrode disposed on said PCB and configured to electrically contact the skin tissue, said at least one surface skin electrode being physically spaced and electrically separate from any needle-like protrusions disposed on the electrode carrier;
    an array of skin-penetrating electrodes disposed on said PCB and configured to electrically contact the skin tissue, each of said skin-penetrating electrodes including a needle-like protrusion;
    an electrical circuit formed or mounted on said PCB and operatively coupled to said at least one surface skin electrode and to each skin-penetrating electrode of said array of skin-penetrating electrodes, said electrical circuit including a pulse generator configured to produce a biphasic pulsed current at the skin tissue via said at least one surface skin electrode and to produce a monophasic pulsed current at each of said skin-penetrating electrodes; and
    a disinfecting mechanism configured to reduce microbial reproduction on said PCB when coupled thereto.

17. The appliance of claim 16, wherein said pulse generator provides said at least one surface skin electrode with pulse trains having a burst frequency of about 0.1 to 10 Hertz, a pulse string frequency within the burst of about 50 to 400 Hertz, a burst duration per each one of said at least one surface skin electrode of up to about 100 milliseconds, a pulse duration of about 0.05 to 0.3 milliseconds, and a current amplitude of up to about 50 milliamperes.

18. The appliance of claim 16, wherein said pulse generator provides said each skin-penetrating electrode with a pulse train of about 0.1 to 10 Hertz, each pulse in said pulse train characterized by a pulse duration of about 0.5 to 10.0 milliseconds and a current amplitude of up to about 2 milliamperes, and wherein said current amplitude during a pulse onset reaches a maximum current amplitude of about 0.5 to 2 milliamperes within about 0.25 milliseconds at most from said pulse onset, said maximum current amplitude being generated by said pulse generator, and wherein said current amplitude is reduced by about 5 to 50 percent thereafter for the remainder of said pulse duration.

19. The appliance of claim 16, wherein the PCB is flexible and conformable to the skin tissue.

20. The appliance of claim 16 further comprising:
   an antimicrobial agent infused within or layered upon said array of skin-penetrating electrodes and within or upon said non-conductive coating thereby to reduce microbial reproduction on each of said skin-penetrating electrodes and non-conductive coating.

21. The appliance of claim 16, wherein said biphasic and monophasic pulsed currents are configured to administer electroanalgesia at said surface skin electrode and at each of said skin-penetrating electrodes in a pattern of transcutaneous electrical nerve stimulation and skin-penetrating electrical nerve stimulation.

22. The appliance of claim 21, wherein said pattern at least one of random, phase-locked, predetermined, and orderly.

23. The appliance of claim 16 further including:
   a rechargeable power source; and
   a recharging mechanism configured to recharge the power source.

24. The appliance of claim 23 further comprising:
   a housing configured integrally to enclose said disinfecting mechanism and said recharging mechanism.

25. The appliance of claim 16, wherein
   the PCB is molded around the array of skin-penetrating electrodes; or
   the array of skin-penetrating electrodes is formed separately and removably attached to the PCB.

26. The appliance of claim 16, wherein
   the at least one surface skin electrode is screen-printed on the PCB; or
   the at least one surface skin electrode is formed separately and removably attached to the PCB.

* * * * *